United States Patent
Prins et al.

(10) Patent No.: US 9,128,084 B2
(45) Date of Patent: Sep. 8, 2015

(54) FAST BIOSENSOR WITH REAGENT LAYER

(75) Inventors: Menno Willem Jose Prins, Eindhoven (NL); Thea Van Der Wijk, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 608 days.

(21) Appl. No.: 12/444,696

(22) PCT Filed: Oct. 10, 2007

(86) PCT No.: PCT/IB2007/054131
§ 371 (c)(1),
(2), (4) Date: Apr. 8, 2009

(87) PCT Pub. No.: WO2008/044214
PCT Pub. Date: Apr. 17, 2008

(65) Prior Publication Data
US 2010/0009456 A1    Jan. 14, 2010

(30) Foreign Application Priority Data

Oct. 12, 2006 (EP) .................... 06122182

(51) Int. Cl.
| G01N 21/00 | (2006.01) |
| G01N 33/558 | (2006.01) |
| G01N 21/64 | (2006.01) |
| G01N 21/65 | (2006.01) |

(52) U.S. Cl.
CPC .......... *G01N 33/558* (2013.01); *G01N 21/6428* (2013.01); *G01N 21/658* (2013.01)

(58) Field of Classification Search
None
See application file for complete search history.

(56) References Cited

U.S. PATENT DOCUMENTS

| 4,503,145 A | 3/1985 | Katsuyama |
| 4,876,067 A | 10/1989 | Deneke |
| 5,260,195 A | 11/1993 | Azhar |
| 5,266,460 A | 11/1993 | Sudo |
| 5,403,706 A | 4/1995 | Wilk |
| 5,607,863 A | 3/1997 | Chandler |
| 6,565,738 B1 | 5/2003 | Henning |
| 6,613,578 B1 | 9/2003 | Moller |

(Continued)

FOREIGN PATENT DOCUMENTS

| CA | 2198520 A1 | 4/1998 |
| CN | 1412321 A | 4/2003 |

(Continued)

OTHER PUBLICATIONS

Gijs, Martin A., Magnetic bead handling on-chip: new opportunities for analytical applications, 2004, Microfluid Nanofluid, vol. 1, pp. 22-40.*

(Continued)

*Primary Examiner* — Robert Xu

(57) ABSTRACT

A detection system (100) and a sensor chip (1) for detecting target molecules, and thus corresponding analytes in a sample is described. Typically the detection system (100) includes a sensor chip (1). The sensor chip (1) comprises on its detection surface (33) a dissolvable reagent layer (5). When the dissolvable reagent layer (5) is in contact with sample fluid, free reagent is generated, assisting in the interaction between a label and target molecules, thus allowing for label based detection. The sample thereby is exposed to mobile reagents in a burst. The reagent layer may contain an enzyme allowing enzymatic assays.

17 Claims, 5 Drawing Sheets

(56) References Cited

U.S. PATENT DOCUMENTS

| | | |
|---|---|---|
| 7,790,439 B2 | 9/2010 | Nadaoka |
| 2001/0024804 A1 | 9/2001 | Shen |
| 2002/0086436 A1 | 7/2002 | Buechler |
| 2003/0109798 A1 | 6/2003 | Kermani |
| 2004/0029177 A1 | 2/2004 | Nadaoka |
| 2005/0003519 A1 | 1/2005 | Jobst |
| 2005/0016844 A1 | 1/2005 | Burke |
| 2006/0003397 A1 | 1/2006 | Knappe |

FOREIGN PATENT DOCUMENTS

| | | | | |
|---|---|---|---|---|
| CN | 1424577 A | | 6/2003 | |
| CN | 1441905 A | | 9/2003 | |
| CN | 1473270 A | | 2/2004 | |
| DE | 4027728 A1 | | 3/1992 | |
| EP | 0238012 A2 | | 9/1987 | |
| EP | 0254457 A1 | | 1/1988 | |
| EP | 0 360 452 | * | 3/1990 | ............. G01N 33/53 |
| EP | 0775484 | * | 5/1997 | ............... A61K 9/00 |
| EP | 1353181 A1 | | 10/2003 | |
| JP | 61284661 A1 | | 12/1986 | |
| JP | 62214356 A | | 9/1987 | |
| JP | 62296897 A1 | | 12/1987 | |
| JP | 63074500 A1 | | 4/1988 | |
| JP | 1047954 A | | 2/1989 | |
| JP | 01231897 A1 | | 9/1989 | |
| WO | 9707243 A1 | | 2/1997 | |
| WO | 0079276 A1 | | 12/2000 | |
| WO | 0208763 A2 | | 1/2002 | |
| WO | 03014740 A1 | | 2/2003 | |

OTHER PUBLICATIONS

Graham, Daniel L. et al "Magnetoresistive-Based Biosensors and Biochips", Trends in Biotechnology, vol. 22, No. 9, Sep. 2004.

Zaytseva, Natalya V. et al "Microfluidic Biosensor for the Serotype-Specific Detection of Dengue Virus RNA", Analytical Chemistry, vol. 77, 2005, pp. 7520-7527.

Richardson, J. et al "The Use of Coated paramagnetic Particles as a Physical Label in a Magneto-Immunoassay", Biosensors & Bioelectronics, vol. 16, 2001, pp. 989-993.

* cited by examiner

FAST BIOSENSOR WITH REAGENT LAYER

FIELD OF THE INVENTION

The present invention relates to the field of biosensors. More particularly, the present invention relates to methods and systems for detecting analytes, e.g. as used in qualitative or quantitative detection of biological, chemical or biochemical particles, and to means for improving such detection methods and systems.

BACKGROUND OF THE INVENTION

Biosensors typically are devices that allow qualitatively or quantitatively detection of target molecules, also called "analytes", such as e.g. proteins, viruses, bacteria, cell components, cell membranes, spores, DNA, RNA, etc. in a liquid, such as for example blood, serum, plasma, saliva, tissue extract, interstitial fluid, cell-culture extract, food or feed extract, drinking water, . . . . In almost all cases, a biosensor uses a surface that comprises specific recognition elements for capturing the analyte. Therefore, the surface of the sensor device may be modified by attaching specific molecules to it, which are suitable to bind the target molecules which are present in the liquid.

One of the measuring principles is the counting of labelled molecules attached at predetermined sites on the biosensor. For example, the molecules may be labelled with magnetic particles or beads and these magnetic particles or beads can be detected with a magnetic sensor. Alternatively, the amount of analyte may be detected by fluorescence. In this case the analyte itself may carry a fluorescent label, or alternatively an additional incubation with a fluorescent labelled second recognition element may be performed.

In most biosensors, a sensor chip is provided with a dry reagent and a detector surface covered with a biologically-active surface coating. The reagent may e.g. comprise labels coupled to biologically-active moieties, e.g. an anti-drug antibody. When the test fluid arrives, the dry reagent dissolves and mixes into the fluid. Thereafter the fluid is transported towards the sensor surface and wets the sensor surface. The labels as well as the sensor are exposed to the drug molecules. This influences the binding of the labels to the sensor surface, which is detected.

Electrochemical biosensors are known, e.g. from US 20050016844 A1, in the form of test strips wherein a dry dissolvable layer is provided near or on the electrodes. The layer generally comprises chemical components for reacting with the analyte or target molecule to produce an electrochemical signal that represents the presence of the analyte in the sample fluid, such as one or more enzymes, co-enzymes, co-factors, buffer salts, and adjuvants to enhance the reagent properties or characteristics such as de- and rehydration. The latter typically is used for detecting analytes present in relatively high concentrations in the sample.

SUMMARY OF THE INVENTION

An object of the present invention is to obtain good methods and systems for detecting biological, chemical and/or bio-chemical particles.

The above objective is accomplished by devices and a method according to the present invention.

The present invention relates to a detection system for detecting at least one target molecule, the detection system having at least one sensor chip and being adapted for receiving at least one label for enabling label detection, the at least one sensor chip comprising a detection surface having at least a first dissolvable layer comprising reagent, the at least a first dissolvable layer being adapted for enabling interaction of the at least one label with the at least one target molecule thus enabling detection of a label based detection signal.

It is an advantage of embodiments of the present invention that fast detection with high sensitivity is enabled using label-based biosensors. It is an advantage of particular embodiments of the present invention that the fast reagent dissolution may be obtained. It is also an advantage of particular embodiments of the present invention that fast mixing of the reagent with the fluid may be obtained. It is also an advantage of particular embodiments of the present invention that the reagent is provided close to the detection region. It is furthermore an advantage of particular embodiments of the present invention that a high concentration of mobile reagent may be obtained in the detection region, allowing achievement of high binding or unbinding rates at the sensor surface.

It is an advantage of particular embodiments of the present invention that handling is easy. Since the sensor chip and the detection system may contain everything needed for detection, no liquids but the sample fluid need to be administered.

It is an advantage of particular embodiments of the present invention that only a very small sample volume for testing is required. It is an advantage of particular embodiments of the present invention that this detection system may contain an array of sensor chips for so-called sensor multiplexing which enables running independent assays in parallel. Different sensors can be used to for multi-analyte detection, e.g. to serve as positive or negative control, for calibration purposes, and/or for parallel screening. It is an advantage of particular embodiments of the present invention that problems of cross-reactivity or cross-contamination are removed or reduced because the reagents have insufficient time to reach neighbouring sensors due to the limited reagent layer thickness and the short duration of the assay.

The detection system may comprise any suitable detector for detecting the at least one label, whereby a magnetic or an optical detector are particularly preferred. It is an advantage of such a system that samples with low analyte concentrations, i.e. for example below 1 mmol/L, may be accurately studied. The detection system may comprise an excitation means for exciting the labels. The excitation means may be an irradiation source. The excitation means also may be a means for generating an electromagnetic field.

The first dissolvable layer may have a thickness in a range having a lower limit of 0.1 µm, preferably 1 µm and an upper limit of 150 µm, preferably 50 µm, still more preferably 15 µm. The thickness referred to in the present application may be the average thickness of the layer. The layer thickness depends on the porosity of the layer, type of assay, speed of dissolution and speed of transport in the fluid (passive transport by diffusion, or active transport by actuation). For porous layers it will be advantageous to use a thicker layer than for less porous layers, in order to have sufficient reagent material on the surface for the biosensor assay. For thicker layers it will be advantageous to apply active transport, in order to expedite the approach of reagent to the sensor surface. For very thin dissolvable layers, the probability of label-to-surface collisions scales favourably with respect to label-to-label collisions in the fluid. A reduction of label-to-label collisions reduces the occurrence of label clustering during the assay, which can improve the quantitative accuracy and reproducibility of an assay with labels such as nanoparticle labels.

The detection system may contain an array of sensor chips for so-called sensor multiplexing. Different sensors can be used, for example, to detect different biological molecules, to serve as positive or negative control, or for calibration purposes. Due to the very thin layer and the short time of the assay, the reagents have insufficient time to reach neighbouring sensors, thereby removing or reducing problems of cross-reactivity or cross-contamination.

The at least first dissolvable layer may be a uniform layer. Alternatively, it may be a non-uniform layer, e.g. consisting of islands, stripes or other structures or patterns. The layer may also be nanoporous and/or microporous to facilitate dissolution. It is an advantage of particular embodiments of the present invention that only small amounts of reagent are required.

The sensor chip further may comprise a second layer for providing capture probes retained or immobilised on the detection surface of the sensor chip. This detection system enables separation of labeled and unlabeled targets by capturing either the bound or the unbound fraction to the detection surface. Working with immobilized capture probes has also the advantage of the ease of multiplexing (i.e. determining different targets at the same time) by a pattern wise deposition.

The capture probes may be adapted for allowing retention or immobilisation of the at least one label or of the result of the interaction of the at least one label with the at least one target molecule. Such retention or immobilisation may be immobilisation on the detection surface of the sensor chip.

The sensor chip further may comprise at least a calibration layer for providing calibration reagents, the calibration layer being a dissolvable layer adapted for enabling calibtration. It is an advantage that an accurate detection system may be obtained thereby. It is furthermore an advantage that a calibration system may be incorporated in a sensor chip of the detection system.

The sensor chip further may comprise a protection layer positioned on top of the at least first dissolvable layer for providing protection, the protection layer being a dissolvable layer. This detection system enables a good preservation and storage of the sensor chip, thus reducing the number of non-usable sensor chips after storage. Multiple layers provide multiple functionality e.g. a buffer layer may be provided that does not contain biologically-active species to suppress any labels from binding to biologically-active species during the fabrication process, or a layer comprising calibration materials, or a cover layer that acts as a protection and lift-off layer against contamination e.g. organic contaminants excreted by surrounding cartridge materials during processing or storage.

The at least one label may be comprised in the at least a first dissolvable layer. It is an advantage of particular embodiments that the sensor chip comprises a limited number of different parts, thus reducing the manufacturing effort needed.

The at least first dissolvable layer of the detection system of the present invention may comprise a dissolvable matrix comprising one or more viscosity modulators, surface tension modulators, adhesion regulators, pH regulators, blocking materials, thickeners, film formers, stabilizers, buffers, detergents, gelling agents, fillers, film opening agents, coloring agents, thixotropic agents, protective agents, or hydrating/dissolving agents. Other dissolvable layers also may comprise such a dissolvable matrix.

The detection system may comprise a sensor chip comprising at least a first layer for enabling rapid dissolution, avoiding clustering of labels within the at least a first layer, preserving the biological activity of the at least one label, and enabling the interaction of the at least one label with the target to occur in optimal or highly favourable conditions.

The detection system of the present invention may comprise at least one reagent which may be or may comprise an enzyme, a co-enzyme, a co-factor, a vitamin, a mineral, an enzyme substrate, or an enzyme inhibitor. This detection system may comprise a sensor chip comprising at least a first layer comprising reagents to enable the interaction of the at least one label with the analyte to occur in optimal or highly favourable conditions. The enzyme may be an activation enzyme.

The reagent may be adapted for reducing a loss of biochemical activity due to folding, shielding, capping or masking. The interaction of the at least one label with the target molecule may be enabled by any suitable assay, e.g. a competition assay, an inhibition assay, a displacement assay, a sandwich assay, an anti-complex assay, an immunoassay, clustering assay, hybridization assay or a blocking assay. It is an advantage of certain embodiments of the present invention that the detection of analytes may be based on the dynamic behaviour of a detection signal.

The detection system further may comprise a sensor for determining the time of arrival of the sample on the detection surface. It is an advantage of such an embodiment that the detection of analytes may be based on the dynamic behaviour of a detection signal.

The detection system further may comprise a sensor adapted for measuring a volume of the sample fluid or part thereof. Such a detection system enables accurate, e.g. quantitative, detection of a target molecule that becomes a detectable label after interaction with a label.

The detection system further may comprise a sensor adapted for measuring the areal density of the at least one label. Such a system enables accurate, e.g. quantitative, detection of a target molecule that becomes a detectable label after interaction with a label.

The at least one target molecule may be a product of an enzymatic conversion.

The detection system further may comprise an analysis means for determining the amount of the at least one target molecule. The at least one target molecule may be indicative of the presence or absence of an analyte in a sample. The at least one target molecule may be identical to the analyte in the sample. The detection system may provide quantitative results. The latter may be obtained by comparing different detection signals detected from the sensor chip.

The analysis means may comprise a calculating means for calculating enzyme kinetics. It is an advantage of embodiments of the present invention that enzyme activity can be studied.

The detection surface may be a porous surface. It is an advantage of embodiments of the present invention that the surface-over-volume ratio can be enhanced.

The at least one label may be a target-specific label. The target-specific label may comprise a target-specific probe. The target-specific probe may be a nucleotide sequence having a sequence complementary to a sequence within said target molecule. The target-specific probe may also be an anti-target antibody.

The at least one label may be bound to the capture probes through a tag such as a biotin tag capable of interacting with another tag such as a streptavidin tag on the capture probes on the detection surface.

The present invention also relates to a method for detecting at least one target molecule in a sample, the method comprising: contacting a sample with a sensor chip comprising at the detection surface at least a first dissolvable layer comprising reagent, allowing interaction between the at least a first dissolvable layer at the detection surface and the sample fluid, thus enabling interaction of at least one label with the at least one target molecule, and detecting of a label-dependent detection signal. The method may furthermore comprise exciting the at least one label, e.g. by irradiating it or by orienting a physical property of the label using an electromagnetic field. The method may also comprise measuring the sensor signal before allowing interaction so as to calibrate the sensitivity of the sensor chip. The calibration may be a calibration for specific label-sensitivity and/or the thickness of the reagent layer. The method furthermore may comprise processing the label-dependent detection signal, e.g. for obtaining an amount or concentration of analyte present in the sample. The method furthermore may comprise separating bound and unbound labels.

The present invention furthermore relates to a sensor chip for detecting at least one target molecule in a sample, the sensor chip being adapted for receiving at least one label for enabling label detection, the sensor chip comprising a detection surface having at least a first dissolvable layer comprising reagent, the at least first dissolvable layer being adapted for enabling interaction of the at least one label with the at least one target molecule thus enabling detection of a label based detection signal. The at least first dissolvable layer may comprise the at least one label. The sensor chip may be disposable.

The present invention furthermore relates to a kit of parts for detecting at least one target molecule in a sample, the kit comprising a sensor chip adapted for receiving at least one label for enabling label detection, the sensor chip comprising a detection surface having at least a first dissolvable layer comprising reagent, the at least first dissolvable layer being adapted for interaction of the at least one label with the at least one target molecule thus enabling detection of a label dependent detection signal, and a predetermined amount of at least one target molecule in a buffer solution. The predetermined amount of at least one target molecule in a buffer solution may serve as a positive control and/or as a standard. The kit may further comprise a buffer solution free of at least one target molecule, provided as negative control.

It is an advantage of particular embodiments of the present invention that the species and concentration levels in the dissolvable layer may be tuned to optimise the desired biochemical processes.

Particular and preferred aspects of the invention are set out in the accompanying independent and dependent claims. Features from the dependent claims may be combined with features of the independent claims and with features of other dependent claims as appropriate and not merely as explicitly set out in the claims.

The teachings of the present invention permit the design of improved methods and apparatus for detecting chemical, biological and/or biochemical particles.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
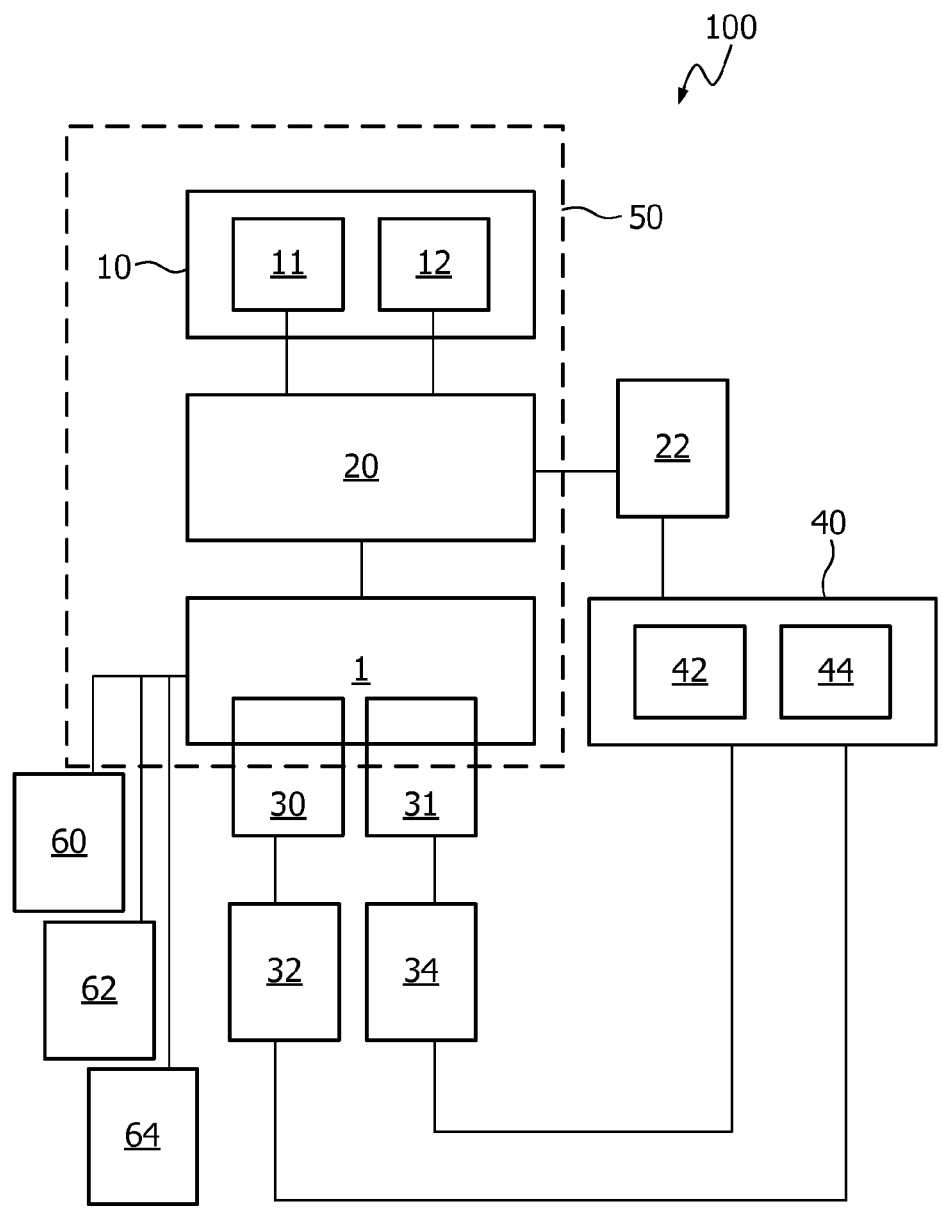
FIG. 1 is a schematic representation of a detection system according to a particular embodiment of the first aspect of the present invention.

In the different figures the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, over and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

The following terms or definitions are provided solely to aid in the understanding of the invention. These definitions should not be construed to have a scope less than understood by a person of ordinary skill in the art.

The term "sample", as used herein, relates to a composition which may comprise at least one analyte of interest. The sample is preferably a fluid e.g. a liquid such as an aqueous composition. Hence, the sample may be provided as a "sample fluid".

The term "analyte", as used herein, refers to a substance whose presence, absence, or concentration is to be determined according to the present invention. Typical analytes may include, but are not limited to, small organic molecules, metabolites such as glucose or ethanol, proteins, peptides, nucleic acid segments, molecules such as small molecule pharmaceuticals, antibiotics or drugs, molecules with a regulatory effect in enzymatic processes such as promoters, activators, inhibitors, or cofactors, viruses, bacteria, cells, cell components, cell membranes, spores, DNA, RNA, microorganisms and fragments and products thereof, or any substance for which attachment sites, binding members or receptors (such as antibodies) can be developed or which have anti-immune or antigenic determinants. Presence, absence or concentration of the analyte may be determined directly by assessing the presence, absence or concentration of the analyte itself, or may alternatively be determined indirectly by assessing the presence, absence or concentration of a target or target molecule.

The term "substrate", as used herein, refers to a molecule or material capable of undergoing an enzymatic reaction.

The term "target" or "target molecule", as used herein, refers to a substance whose presence, absence, or concentration is actually determined according to the present invention. The term "target molecule" should be construed broadly and can be, for example, an individual molecule, can be a cluster of molecules, can be a complex of molecules, can be a molecule embedded in other material such as a substrate, etc. The target and analyte may be identical, or the target may be indicative of the presence or absence of the analyte. In particular, targets such as proteins or DNA may be a distinctive component or product of analytes such as viruses, bacteria, or other organisms, and therefore indicative of their presence. Where detection involves an enzymatic assay, the target may be a product of an enzymatic conversion of a substrate by an enzyme, and may therefore be indicative of the amount of substrate or the activity of the enzyme. Target molecules may also be polymers, metal ions, and low molecular weight organic species such as toxins, illicit drugs, and explosives, the invention clearly not limited thereto. During the detection assay, the target may become labelled to emanate a detectable signal. The target may also become immobilized on the detection surface as part of a biologically-active coating.

The term "label", as used herein, refers to a molecule or material capable of generating a detectable signal. Generating a detectable signal includes change of a signal. Suitable labels for use in the different detection systems and methods of the present invention are numerous and extensively described in the art. These may be optical labels, radioactive labels, magnetic labels, etc. Labels can be direct labels, which can directly be detected by a sensor. Alternatively, labels can be indirect labels, which become detectable after a subsequent development process. Typically, the label used in the methods of the present invention is a target-specific label, i.e. capable of binding specifically to the target. Nevertheless it is also envisaged that where the target is present in a purified form, it is sufficient that the label binds to the target.

The term "probe", as used herein, refers to a binding molecule that specifically binds a target molecule. Probes envisaged within the context of the present invention include biologically-active moieties such as whole antibodies, antibody fragments such as Fab' fragments, single chain Fv, single variable domains, VHH, heavy chain antibodies, peptides, epitopes, membrane receptors or any type of receptor or a portion thereof, substrate-trapping enzyme mutants, whole antigenic molecules (haptens) or antigenic fragments, oligopeptides, oligonucleotides, mimitopes, nucleic acids and/or mixtures thereof, capable of selectively binding to a potential target molecule. Antibodies can be raised to non-proteinaceous compounds as well as to proteins or peptides. Probes are typically members of immunoreactive or affinity reactive members of binding-pairs. The nature of the probe will be determined by the nature of the target to be detected. Most commonly, the probe is developed based on a specific interaction with the target such as, but not limited to, antigen-antibody binding, complementary nucleotide sequences, carbohydrate-lectin, complementary peptide sequences, ligand-receptor, coenzyme-enzyme, enzyme inhibitors-enzyme, etc. Probes also include "capture probes" for immobilizing targets and/or labeled targets on the detection surface via recognition or binding events. Probes and capture probes may be labeled. Where a target molecule is immobilized through binding to a capture probe the resulting complex is referred to as a "target-capture complex". Where the label used in the devices and methods of the present invention is a target-specific label, this can be ensured by using a target-specific probe bound to a label. Typically, where the target is a protein, the target-specific probe can be an anti-target antibody. Alternatively, where the target is a nucleotide sequence, the target-specific probe can be a complementary oligonucleotide sequence. The term "target analogue", as used herein, refers to a substance that can associate with a probe or capture probe less optimally than the target. The target analogue is used in competitive assays where the target is determined based on competition with the target analogue, e.g. in the competitive binding to a probe or capture probe. In particular, the target analogue binds to a probe or capture probe with a reduced binding strength compared to the binding of the target to probe or capture probe.

According to a first aspect, the present invention provides a detection system for detecting and/or quantifying at least one target molecule, and thus an analyte, in a sample. Such a detection system may be for example a detection system for detecting chemical, biological or bio-chemical particles, the invention not being limited thereto. The detection system typically is for use with at least one sensor chip, adapted for receiving at least one label for enabling label-based detection. The sensor chip furthermore has a detection surface comprising at least a first layer, the first layer being a dissolvable layer for providing at least one reagent for enabling interaction of the at least one label with the at least one target thus enabling detection of a label-based detection signal. The dissolvable layer may be referred to as dissolvable reagent layer, although besides reagent also other components may be present in the layer. The term "dissolvable layer", as used herein, may refer to a layer consisting of a dissolvable matrix and optionally labels, probes, labelled probes, target, and/or target analogues. When the dissolvable reagent layer is contacted with sample fluid, the sample is preferably exposed to mobile reagents in a burst, i.e. during a short time.

A schematic overview of a detection system 100 comprising essential and optional components is shown by way of illustration in FIG. 1. The detection system 100 is suitable for detecting and/or quantifying at least one target molecule, and thus an analyte, in a sample. The system 100 is suitable for detecting and optionally quantifying the presence of a target molecule, or derived therefrom an analyte in a sample, whereby the provision of a dissolvable layer comprising reagent on the detection surface of the sensor chip enables fast detection of a label as a direct or indirect indication of the presence or activity of the analyte. As shown in FIG. 1, the detection system 100 is adapted for use with at least one sensor chip 1. These and other additional or optional components of the exemplary detection system 100 as shown in FIG. 1 will be further described in more detail below. The sensor chip 1 will be described, with reference to FIG. 2 and FIG. 3 by way of illustration, the sensor chip 1 not being limited thereto.

The sensor chip 1 may comprise several components such as a chip carrier 2 having a surface 3. At least part of the surface 3 may be adapted for being a place of detection using a detector 30. In other words, the surface 3 may comprise a detection surface 33, where label-based detection may be performed. The chip carrier 2 may be made of a material allowing the chip carrier 2 to support the different components present in and/or on the chip carrier 2. It may comprise an insulating material, although the invention is not limited thereto. Plastics such as vinyl polymers, polyimides, polyesters, and styrenes can provide the structural properties which are required. As the sensor chip is preferably mass producible, it may e.g. be made from material that has sufficient flexibility for roll processing, while also giving a useful stiffness to the finished chip. The chip carrier 2 therefore may comprise a flexible organic material, e.g. a polymeric material such as polyester, especially high temperature polyester materials, polyethylene naphthalate (PEN), and polyimide, or mixtures of two or more of these. Another particularly preferred chip carrier material is an inorganic material, e.g. a semiconductor material such as silicon, or a material such as glass.

The surface 3 of the sensor chip 2 typically may comprises a carrier chip material to which a biologically-active layer of capture probes, targets or target analogues may be attached or onto which a biologically-active layer is immobilized. The surface 3 of the sensor chip 2 can be a porous surface in order to enhance the surface-over-volume ratio.

The term "biologically-active coating" may refer to a layer of biologically-active moieties such as capture probes and/or target molecules that are retained by or attached to a solid surface such as the detection surface of the sensor chip, and that are capable of binding, or that are reactive with, a target or a labelled probe, respectively. The capture probes and/or target molecules of the biologically-active layer may be retained or immobilized on the surface by any method known in the art. These biologically-active moieties may be retained by, or attached to the detection surface in a site-specific manner meaning that specific sites on these moieties are involved in the coupling, e.g. through a protein-resistant layer on the substrate. Alternatively the surface 3 may comprise a metal layer e.g. a noble metal layer that covers the carrier chip or a portion thereof.

According to embodiments of the present invention, the surface 3 of the carrier chip 2 comprises at least one dissolvable layer comprising reagent, also referred to as dissolvable reagent layer 5, assisting in label-based analyte detection. Such a layer may be a dry layer. Generally, the at least one reagent layer 5 of the sensor chip 1 may comprise reagents of chemical or biochemical nature for reacting with the target to produce a detectable signal that represents the presence of the analyte in the sample. The term "reagent", as used herein, is a chemical, biological or biochemical reagent for reacting with the analyte and/or the target to produce a detectable signal that represents the presence of the analyte in the sample. Suitable reagents for use in the different detection systems and methods of the present invention include a variety of active components selected to determine the presence and/or concentration of various analytes. The selection of appropriate reagents is well within the skill in the art. As is well known in the art, there are numerous chemistries available for use with each of various targets. They are selected with respect to the target to be assessed. The reagent may contain for example an enzyme, a co-enzyme, an enzyme inhibitor, an enzyme substrate, a co-factor such as ATP, NADH, etc. to facilitate enzymatic conversions, a vitamin, a mineral, the invention not being limited thereto. For example, in one preferred embodiment, the sensor chip of the present invention can include one or more enzymes, co-enzymes, and co-factors, which can be selected to determine the presence of metabolites or small molecules in a sample. Furthermore, the at least the first layer of the sensor chip 1 may further contain labels, buffer salts, detergents, sugars, etc.

The at least one reagent layer 5 may be a thin layer. The at least one reagent layer 5 should be sufficiently thin such that the sample fluid will hydrate or dissolve the thin reagent layer 5 rapidly. Preferably, the at least one reagent layer 5 may have a thickness in a range having a lower limit of 0.1 μm, preferably 1 μm, and an upper limit of 150 μm, preferably 50 μm, still more preferably 15 μm. The thickness referred to in the present application may be the average thickness of the layer. The reagent layer 5 may be a substantially uniform layer, or it may comprise structures or patterns such as an island or stripe structure, or may be alternatively or additionally porous to improve its dissolution. The thickness then refers to the average thickness of the material in the patterns, structures, islands or stripes, etc. The reagent layer may also be a porous material to facilitate dissolution, such as e.g. a microporous and/or nanoporous layer. During manufacturing, the reagent layer may be for example provided on a cooled substrate to reduce interaction between the reagent layer and the detection surface at the moment of manufacturing. The reagent layer may for example also be provided using lyophilisation. In a preferred embodiment, labels 6 are comprised within the reagent layer 5 and will diffuse through and within the reagent layer 5 to the detection surface 33 upon contacting the latter with the sample fluid. The labels 6 will have a short distance to diffuse through a thin reagent layer, therefore, diffusion to the detection surface 33 will occur quickly. Additionally, the capture efficiency will be greater for a thin than for a thick layer. A thick reagent layer will take more time for the sample fluid to hydrate or dissolve, and more time will be needed for the reagent or labels 6 to approach the detection surface 33. This can delay the time to determine the analyte concentration and introduce errors into the determination. When a relatively thick layer is used, it is advantageous to apply active transport, in order to expedite the approach of reagent to the sensor surface.

By way of illustration, whereby embodiments of the invention are not limited by theory, a suitable thickness of a dissolvable reagent layer 5 can be determined based on the diffusion law. The rapid dissolution and diffusion of reagents is a burst process. When diffusion is the dominant transport mechanism (i.e. active materials transport is not used), a suitable layer thickness L can roughly be estimated as follows:

$$L \approx \sqrt{(D \cdot t)}$$

with D the diffusion constant of the reagent in the dissolved layer, and t the desired reaction time. In other words, a suitable layer thickness L may be approximated by the square root of the product of the diffusion constant of the reagent in the dissolved layer D and the desired reaction time t. The diffusion constant D will generally be different for different (bio)chemical species. When D is of the order of $10^{-10}$ $m^2 \cdot s^{-1}$ once the reagent is released into the fluid, e.g. for a small protein functioning as an enzyme substrate, and the desired reaction time is 1 s, a suitable layer thickness L is about 10 µm. A much thinner layer will give a strong time dependence of the reagent concentration during the reaction process. A much thicker layer consumes an unnecessarily high quantity of reagent and furthermore generates a distribution of target molecules that is further away from the detection surface. When the reagent in the reagent layer 5 is coupled to a larger entity e.g. to a nanoparticle with a size of 300 nm, D is of the order of $10^{-12}$ m$^2 \cdot$s$^{-1}$. With a desired reaction time of 10 s, a suitable layer thickness L is about 3 µm. In an embodiment wherein labels 6 are comprised in the reagent layer 5, a similar consideration can be made. If diffusion is the dominant transport mechanism, the burst or diffusion time thus can be approximated by $$T_b \approx L^2/D,$$

with L the thickness of the layer (unit: m) and D the diffusion constant of the labels in the fluid (unit: m$^2 \cdot$s$^{-1}$) and $T_b$ the diffusion time of the layer, whereby for simplicity the enhanced friction due to the presence of the surface is neglected. For example, labels such as nanoparticles with a diameter of 300 nm in a aqueous fluid typically may have a diffusion constant D of the order of $10^{-12}$ m$^2 \cdot$s$^{-1}$. With a layer thickness L of 3.2 µm, the estimated diffusion time $T_b$ is about 10 seconds. From this, it becomes apparent that the burst time $T_b$ depends on the square of the distance, which emphasizes the importance of using an ultra thin layer if shorter detection times want to be achieved.

The speed of the test is furthermore limited by the association rate between target and capture probe. For a given capture probe such as an antibody, the probability p that a target-capture complex, e.g. an antigen-antibody bond, is formed increases linearly with time t in the limit p<1. The probability increase per unit time dp/dt is given by $$dp/dt = k_{on} \cdot [T],$$

with $k_{on}$ the association constant of the binding of the target molecule to the capture probe (unit: L·mol$^{-1} \cdot$s$^{-1}$) and [T] the target concentration in the fluid (unit: mol·L$^{-1}$). For example, $k_{on} = 10^5$ L·mol$^{-1} \cdot$s$^{-1}$ for a drug-antibody bond and [T]=100 nmol·L$^{-1}$ give dp/dt=0.01 s$^{-1}$. This means that with above chosen parameters a target-capture complex is formed after 10 s with a probability of 10%.

The at least one dissolvable reagent layer 5 of the sensor chip 1 may comprise a dissolvable matrix 7 or a dried porous material holding reagents and/or labels and/or a variety of adjuvants to enhance the reagent properties or characteristics and/or protective agents to preserve the components within the dissolvable layer 5 during processing, storage, and handling. Matrix 7 typically may promote rapid dissolution, avoid clustering of labels, and preserve the biological activity of moieties. The chemistry may include materials to facilitate the placement of the reagent composition onto the surface 3 of the carrier chip 2 and to improve its adherence to the carrier chip surface 3, or for increasing the rate of hydration of the reagent composition by the sample fluid. Additionally, the reagent layer 5 can include components selected to enhance the physical properties of the resulting dried reagent layer, and the uptake of a liquid test sample for analysis. Examples of adjuvant materials to be used with the reagent composition include viscosity modulators, surface tension modulators, adhesion regulators, pH regulators, blocking materials, thickeners, film formers, stabilizers, buffers, detergents, gelling agents, fillers, film openers, coloring agents, agents endowing thixotropy, silica, and agents facilitating dissolving and hydration.

The sensor chip 1 preferably comprises actuation means for actuating the liquid wherein the envisaged reaction takes place. This actuation is for example advantageous to improve the speed, precision, sensitivity and/or specificity of the test, by mixing of reagent in the fluid, by transport and/or upconcentration of reagent to a detection region, and by applying stringency, e.g. via washing or via electromagnetic stringency forces. Therefore actuation is preferably used to prepare reagents in proximity to a biosensor chip. A highly preferred method of actuation is based on magnetic actuation. Magnetic actuation is possible when probes or other compounds that play a role in the reaction that is monitored, are linked to a magnetic particle, and/or when non-reacting magnetic particles are added to the reaction chamber. Therefore in a highly preferred embodiment, the sensor chip 1 and/or the reader system comprise at least one magnetic actuation part such as an electromagnet or current wire for creating a magnetic field close to the sensor surface. If magnetic actuation is used, the detection may still be via magnetic detection and/or optical detection using in addition an optical label. This is described in more detail below.

The sensor chip 1 typically is adapted for receiving at least one label for label based detection after interaction with the target molecule. In a preferred embodiment the labels may be provided in at least the first dissolvable layer. Alternatively, the labels may be attached to the detection surface as a so-called second dissolvable layer. The labels may also be provided from outside the sensor chip, e.g. as an aqueous fluid containing labels in an appropriate concentration, or as part of the sample fluid. The labels may also be provided from another position in the detection chamber or the cartridge, preferably controlled by an actuation mechanism. The label(s) are provided for interaction with the target molecule which may typically be through a binding assay. Through the use of labelled binding molecules, the binding or recognition events may typically generate a detectable signal and indicate the presence or absence or activity of a target molecule. Binding and unbinding assays as envisaged in the present invention include immunoassays, DNA hybridization assays, and receptor-based assays that are widely used in the medical community as diagnostic tests for a wide range of target molecules. Possible assays also include sandwich assays, anti-complex assays, and blocking agent assays, see for example "The Immunoassay Handbook" published by Elsevier Science and edited by David Wild. In a sandwich assay using bead probes 61 the labels 6 typically are kept close to the detection surface 33 e.g. by electric and/or magnetic fields, so that the bead probes 61 attach to the detection surface 33 for the formation of molecular sandwich structures while targets are interacting with bead probes 61 and detection surface 33. The various types of (un)binding assays may use optical labels such as e.g. fluorescent, chromogenic, scattering, absorbing, refracting, reflecting, SERRS-active or (bio)chemiluminescent labels, molecular beacons, may use radioactive labels, may use enzymatic labels or may use magnetic particles as labels. Optical labels typically may emit light detectable by a detector, e.g. in the visual, infrared or ultraviolet wavelength region. Nevertheless, the invention is not limited thereto and optical labels, in the present application, may refer to labels emitting in any suitable and detectable wavelength region of the electromagnetic spectrum. Magnetic labels envisaged within the context of the present invention include, but are not limited to, metal or magnetic beads or nanoparticles. The magnetic label may include any suitable form of one or more magnetic particles e.g. magnetic, diamagnetic, paramagnetic, superparamagnetic, ferromagnetic that is any form of magnetism which generates a magnetic moment in a magnetic field, either permanently or temporarily. Examples of suitable magnetic label material are e.g. $Fe_3O_4$ beads. The size of the magnetic label is not critical in most embodiments but for many biosensor applications it is highly preferred that the labels are of a small size. Preferred magnetic labels may have a size, generally expressed by the longest diameter, in the range 5 to 5000 nm, more preferred 10 to 2000 nm, even more preferred 20 to 1000 nm, still more preferred 50 to 500 nm. Detection of a magnetic label is generally done by application of an electric, or magnetic, or electromagnetic field and using a magnetic or non-magnetic sensor. Unless specified the label refers to the molecule or material as such, not covalently linked to a probe. The label may be attached to a probe, a capture probe, a substrate, a target, or an analyte, preferably through covalent binding but other types of binding such as hydrogen binding are also possible. Depending on the type of assay being performed, labelled target molecules either bind to immobilized capture probes (sandwich assay), or compete with target analogues to bind to capture probes (competitive assay). After removal of excess (unbound) label, the amount of bound label is measured. Thus, binding assays may typically involve adherence of labelled binding molecules to a solid substrate in numbers that reflect the concentration or presence of the target molecule. Alternatively, labelled binding molecules such as labelled target analogues may be bound to the detection surface and the displacement of labelled target analogues by target molecules may result in a decrease of labels near the detection surface. A large number of variations on binding assay methodologies have been described and are all within the scope of the present invention.

In the sensor chip 1, e.g. possibly on the detection surface 33 thereof, additional layers may be provided, e.g. a layer functioning as protection layer, a calibration layer or a buffer layer. A protection layer may allow protection of particular parts of the sensor chip 1 against internal or external chemical or mechanical influences. A calibration layer typically may be used for calibrating the sensor chip with respect to the specific label used, the layer thickness used, etc. One can add for example a known amount of target molecules or target-like molecules to a dissolvable layer on the sensor chip for obtaining such calibration. The latter thus may allow for on-chip assay calibration. Furthermore a positive test control layer and/or a negative test control layer may be provided. Such layers typically may provide the necessary components for checking the sensor chip such that it should provide a definite positive and/or definite negative response, thus allowing a quality check of the sensor chip 1. A buffer layer typically allows buffering between two different layers that should not or initially should not interact with each other. More detailed examples of such layers will be discussed in more detail in the different embodiments.

The sample fluid that is to be contacted with the detection surface may exert hydrophilic/hydrophobic forces on the detection surface (33) to be wetted. An additional protection layer may be provided to give protection to the forces introduced by the sample fluid.

In order to detect the label-based signal, the detection system 100 may further comprise at least one detector 30 for detecting labels on or near the surface of the sensor chip 1. Such a detector 30 of the detection system 100 thus may be able to detect labels or more particularly the response to an excitation thereof at the detection surface 33. The detector 30 may be incorporated in the chip carrier 2, thus typically resulting in a lab-on-chip biosensor, or it may be incorporated in the detection system 100, adapted for comprising the sensor chip 1. Alternatively, the detection system may be a stand-alone system that is moved to the relevant position to detect the detection surface of the chip carrier. In a lab-on-chip set-up, the active elements of the detector 30 can be positioned in the chip carrier 2 of the sensor chip, whereas the detected signal may be converted and transferred to a read-out device external to the sensor chip 1. Alternatively, the active elements of the detector 30 may be positioned in the detection system 100 outside the sensor chip. The detector 30 then is adapted to detect a signal from the detection surface 33. For example in optical detection, the latter may be obtained by focussing on and collecting from the detection surface 33.

The at least one detector 30 may be any suitable detector, e.g. an optical detector for optically detecting labels, such as optical and/or magnetic labels, and/or a magnetic detector for detecting magnetic labels. An optical detector, for detecting optical signals e.g. luminescent signals from optical labels or indirect luminescent labels from magnetic labels, may e.g. be a photodetector, a charged coupled device (CCD), a charged injection device (CID), a complementary metal-oxide semiconductor (CMOS), a photomultiplier tube, an avalanche photodiode, a solid state optical detection device, a microscope or a video camera. The at least one detector 30 may be a number of detectors, adapted for detecting different luminescence irradiation beams collected from the sensor chip 1. The at least one detector 30 may be a pixelated detector or a line of multiple single-pixel detectors. Such a detector may e.g. be a charge coupled device (CCD) detector or a CID, a row of photon tube multipliers, a row of avalanche photodiodes or an other irradiation detector that comprises an array of individual detector pixels. The width of the at least one detector 30 or, in case pixelated detectors are used, of the detector elements of the at least one detector 30 preferably may be such that detection may occur of the whole sensor chip 1 or sensor chips, or of spatially distinctive areas on the sensor chip 1, whereby the spatially distinctive areas are such that approximately always maximally one strip or spot of reagent layer(s) is present within the area detected by a single pixel during examination allowing to detect whether or not a strip or spot of reagent layer(s) 5 leads to label detection or not when in contact with sample fluid.

The at least one detector 30 may also be a magnetic detector such as e.g. a Hall detector or a magneto-resistive detector such as e.g. an AMR (anisotropic magneto-resistance) detector, a GMR (giant magneto-resistance) detector, or a TMR (tunnelling magneto-resistance) detector. Magnetic sensor elements based on other principles such as SQUIDS are also possible for application in the claimed detection system 100. The detector 30 may also be based on other principles for detecting magnetic particles and may therefore also be a force amplified biological sensor (FABS), a cantilever-beam force transducer, a microbalance, an impedance meter, or an AFM wherein forces from/on magnetic particles are detected. The detection of magnetic beads can also occur based on optical principles such as refraction, absorption, scattering, fluorescence, etc. As such, detector 30 may be an optical detector for detecting magnetic particles. Typically, the detector 30 may be connected to detector driving circuitry 32 for driving the detector 30. The detector driving circuitry 32 typically may be adapted for controlling the detector 30. It typically may be adapted for being positioned outside the chip carrier 2, even for being positioned outside the sensor chip 1, and for being connectable to the detector 30. Nevertheless, it also may be included in the chip carrier 2 or in the sensor chip 1. The detector may be adapted, e.g. in position or by providing additional focusing components, for detecting labels or a detectable signal thereof at a detection surface 33.

The detection system 100 furthermore may comprise an excitation means 31 adapted for exciting the labels used. Depending on which labels used, the excitation means 31 may e.g. be an optical excitation means or a magnetic excitation means. The excitation means 31 may be controlled by an excitation means driving circuitry 34. It typically may be adapted for being positioned outside the chip carrier 2, even for being positioned outside the sensor chip 1, and for being connectable to the exciation means 31. Nevertheless, it also may be included in the chip carrier 2 or in the sensor chip 1. An optical excitation means may e.g. be an irradiation unit comprising one or more irradiation sources for generating an irradiation beam for irradiating a sample on a sensor chip containing optical labels. The at least one irradiation means 31 may be any irradiation source suitable for use in an optical detection system, such as e.g. a light source. The irradiation means 31 also may comprise a white light source which may be filtered to several irradiation beams having radiation at a specific wavelength or in a specific wavelength range. The irradiation means 31 also may comprise one or more monochromatic optical sources such as lasers. The irradiation means 31 may comprise argon lasers, diode lasers, helium lasers, dye lasers, titanium sapphire lasers, Nd:YAG lasers or others. The irradiation means 31 may for example comprise a tuneable irradiation source, such as e.g. a tuneable semiconductor laser, for consecutively supplying at least one irradiation beam, or at least one semiconductor laser for simultaneously or consecutively supplying at least one radiation beam. A plurality of irradiation means 31 may be provided allowing multiplexing. The irradiation unit may be adapted for generating electromagnetic radiation suitable for exciting the optical labels. For example, in the case where the generated irradiation is fluorescence irradiation, the optical wavelength of the excitation irradiation typically may be e.g. in the range from 200 nm to 2000 nm, or e.g. in the range from 400 nm to 1100 nm, the invention not being limited thereto. The latter may be incorporated in the chip carrier 2 or may be external thereto and it may be incorporated in the sensor chip 1 or may be external thereto. A magnetic excitation means may e.g. be an electromagnetic unit for generating an electromagnetic field for applying an electric or magnetic field to a sample containing magnetic labels in order to orientate the magnetic beads. The magnetic excitation means 31 may e.g. be a magnetic field generator that creates a magnetic field for magnetizing and orientating the magnetic labels. The magnetic excitation means may be incorporated in the chip carrier 2 or may be external thereto and it may be incorporated in the sensor chip 1 or may be external thereto. The magnetic excitation means may be for example may be an electromagnet, an air-cored wire coil, a straight wire, a conductive micro-fabricated trace, a permanent magnet. a coil. It may be an external magnetic excitation means or it may be integrated in the chip carrier 2.

As mentioned above, the detector 30, the excitation means 31 and/or the driving circuitry thereof 32, 34 may optionally be external to the sensor chip, or even external to a cartridge 50 comprising the sensor chip 1 and means for providing sample fluid 20 and/or means adapted for containing sample fluid 11 or a means adapted for containing test fluid 12. If the detector 30 or the excitation means 31 is outside the cartridge 50, windows may be provided in the cartridge 50 so that the detection unit 30 may detect the sample, etc.

Signals representative of the detections may be supplied to an analysis circuitry 40 which can be adapted to carry out any of the analysis algorithms of the present invention described above.

The detection system 100 may further comprise an analysis circuitry 40 adapted for processing detection signals or signals corresponding therewith. It typically may be adapted to carry out predetermined algorithms for processing the obtained detector results. The analysis circuitry 40 may be adapted for determining a concentration or distribution of an analyte in a sample and/or for processing the obtained detection results e.g. to determine enzyme activity. Thereto, the analysis circuitry 40 conventionally includes a connection with the detection unit 30 to evaluate the detection signal corresponding to the concentration of the target. The concentration of analyte(s) may be calculated by comparing the detection signals detected from the sensor chip, e.g. at different time points in the provision of sample to the sensor chip 1. The analysis circuitry 40 may provide a digital binary value indicating whether or not a labelled target is present. The system 100, and more particularly the analysis circuitry 40 may further provide statistical processing of the obtained detection results, e.g. to correlate two different measurements for checking whether or not lightly bounded labels have influenced the detection. The analysis circuitry 40 may also include means for determining that the sample has been received by the sensor, and that the amount of sample is sufficient for testing. The analysis circuitry 40 may comprise a processing means 42, such as e.g. a microprocessor, and/or a memory component for storing the obtained and/or processed evaluation information. Furthermore typical input/output means may be present. The analysis circuitry 40 may be controlled using appropriate software or dedicated hardware processing means for executing the evaluation steps. The analysis circuitry 40 may thus be implemented in any suitable manner, e.g. dedicated hardware or a suitably programmed computer, microcontroller or embedded processor such as a microprocessor, programmable gate array such as a PAL, PLA or FPGA, or similar. The analysis circuitry 40 typically may store and display the results of the analysis on any suitable output means 44 such as a visual display unit, plotter, printer, etc. or may alternatively provide the data to a separate device. The analysis circuitry 40 may also may have a connection to a local area or wide area network for transmission of the results to a remote location. Analysis circuitry 40 may be at least partly in the cartridge 50 or may optionally be external to the cartridge 50. The analysis circuitry 40 may be connected to the cartridge 50 by suitable contacts on the surface of the cartridge, e.g. terminals.

The detection system 100 may further comprise a fluid containing means 10 for containing fluids, e.g. sample fluid, which can be provided as one or more containers functioning as sources for the detection system. Such fluid containing means 10 for containing fluids may be at least one means 11 adapted for containing sample liquid to be studied, i.e. a specialised source 11 of sample suspected of containing an analyte. The fluid containing means 10 for containing fluids optionally also may comprise at least one means 12 adapted for containing a control sample, e.g. a sample containing a predetermined concentration of an analyte or a target serving e.g. as a positive control or as a reference sample, and/or a sample not containing the analyte or target under investigation e.g. a blank or a negative control. The sample is preferably a fluid sample. An aqueous composition is highly suitable for use in this detection system. Optionally, when the label is provided separately, the detection system 100 may further comprise at least one source of label, not shown in FIG. 1.

The detection system 100 may further comprise a sample providing means 20 for providing sample from the fluid containing means 10 for containing sample to the sensor chip 1 e.g. for contacting the sensor chip 1 with the sample fluid. The sample providing means 20 may include gravimetric feeds of the fluid and may also include an arrangement of pipes/conduits and valves, e.g. selectable and controllable valves, to allow the provision of the fluids from a means 11 for containing sample fluid and a means 12 for containing a control sample to the sensor chip 1. Alternatively, the fluids may be actively or passively pumped from the means 11, 12 to the sensor chip 1. The above arrangement of components may be located on a cartridge 50, e.g. a disposable cartridge 50. Control circuitry 22 for controlling the sample providing means 20 also may be present.

The detection system 100 optionally may further include a dissolution facilitating means 60 to assist dissolution of the dissolvable layer(s) and diffusion of dissolved components on or near the sensor chip 1. The dissolution facilitating means 60 may comprise a magnetic actuator, a heater, or any other suitable mechanic or acoustic means to facilitate dissolution and diffusion.

The detection system 100 optionally may further include a temperature control means 62 to control the temperature for ensuring appropriate temperatures on or near the sensor chip 1. The temperature control means 62 may comprise a heating and/or cooling element thus allowing control of the temperature of the sensor chip 1 or the sample fluid present in the sensor chip 1. The temperature control means 62 may be internal or external to the sensor chip 1, it may be internal or external to the cartridge 50. Heating and cooling elements useful within detection systems as mentioned herein may come in various forms, including but not limited to electric heaters, resistive heaters, thermoelectric heaters and coolers (Peltier devices), capacitively coupled RF heaters, heat sinks, fluidic circuit heaters, heat pipes, chemical heaters, and other types. In certain embodiments, fluid within a detection system 100 is heated using an off-board heating mechanism. Radiative heating may also be applied. The temperature control means 62 typically also may comprise a temperature sensor, for determining a temperature of the detection surface 33 or the sample near that detection surface 33.

The detection system 100 optionally also may comprise a cleaning means 64, for cleaning the detection system or part thereof, such as e.g. the sensor chip 1 or the detection surface 33 in the sensor chip 1. The cleanability of the detection system 100 generally depends on the presence of smooth surfaces. Surfaces in contact with biologically-active compounds may preferably be smooth, accessible for cleaning solutions, and easily rinsable. The choice of materials for the detection system parts to be resistant in a wide pH range enables the use of customary cleaning solutions for biological materials, often having extreme pH values. The cleanability of surfaces also includes their sterilizability. In the case of planar systems, UV sterilization is suitable in particular, but presupposes corresponding UV stability. The choice of UV stable materials composing the sensor chip 1 enables a UV irradiation treatment for sterilization prior to use.

The detection system 100 optionally may further include a sensor for measuring the volume as well as areal density of the label containing fluid on the biosensor surface. The latter may e.g. be performed using an optical measurement, a pressure measurement, by measuring the volume in the means for providing fluid 10 or by measuring the presence of fluid and or flow rate of fluid in different parts of the fluid providing means 20. The time of arrival of the fluid on a sensor surface can also be determined by e.g. capacitance or temperature changes. The latter may provide additional information about the response time of the luminescent labels and/or may be used as input for controlling the detector 30, of the excitation means 31 or as feed-back signal to the controller 22 for controlling the fluid providing means 20. The time of arrival of the fluid on the detection surface 33 also may be taken into account by the analysis circuit 40.

An actuator adapted for further stimulating interaction of the at least one label with the at least one target molecule also may be present. Such an actuator may be a magnetic, electric or acoustic field. This may enhance the dynamics of the assay by speeding up the binding kinetics. An actuator may also be applied for a removal or stringency process to enhance the specificity and sensitivity of the assay.

A sensor chip 1 may contain an array of sensors, for so-called sensor multiplexing. Different sensors can be used to detect different biological molecules, they can be used as positive or negative control, or can be used for calibration purposes. In state-of-the-art biosensors, different sensors are generally exposed to the same reagents. This gives problems of cross-reactivity or cross-contamination, for example because the same labels can bind to different sensor surfaces. Due to the limited amount of reagents provided, as the reagent layer typically may be thin, and due to the short time of the assay, in particular embodiments of the present invention, the reagents typically may have insufficient time to travel to neighbouring sensors on the substrate. The travel distance will be about $(D.t)^{1/2}$, with D the diffusion constant and t the time. Due to the short time, the reagents thus will not reach neighbouring sensors, removing problems of cross-reactivity and cross-contamination. This enhances the multiplexing potential of the biosensor.

The present invention thus also allows for screening of a sample. A non-limiting example of a screening assay is the following. A series of sensors is provided with reagents, characterized in that the reagents are different in the fact that a different (bio)chemical component is missing, and that the sensor gives a positive signal when the sample supplies the missing component, and that the sensor gives a negative signal when the sample does not contain the missing component. For example, in this way a sample can be screened for the presence of co-factors.

Further embodiments and examples according to the first aspect are provided below.

Figure 6:
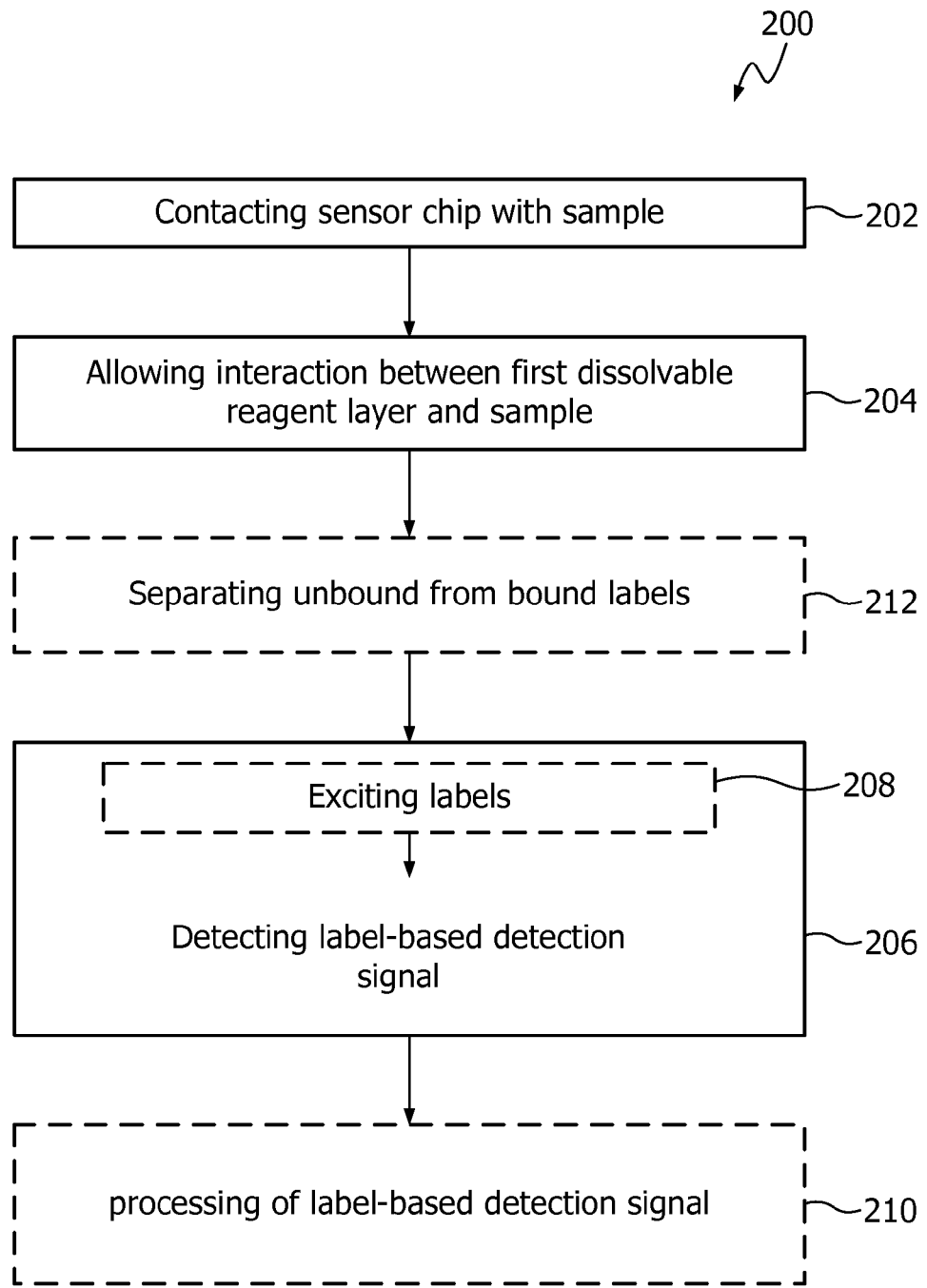
FIG. 6 is a flow diagram of a method for detecting target molecules in a sample according to a third aspect of the present invention.

According to a second aspect, the present invention provides a method for detecting at least one target molecule in a sample. The latter typically also may allow to quantify target molecules in a sample. Such a method for detecting a target typically comprises contacting a sample with a sensor chip 1 comprising at least a first, dissolvable layer with reagent. Typically, the method furthermore comprises allowing interaction between the at least a first dissolvable reagent layer and the sample fluid, resulting in dissolving of the first dissolvable reagent layer and in the interaction of the at least one label with the at least one target molecule. The latter is illustrated by way of example in FIG. 6, indicating a flow diagram of a method 200 according to the second aspect of the present invention, indicating standard and optional steps of an exemplary detection method.

In a first step 202, the sample and sensor chip 1 comprising at least a first dissolvable reagent layer 5 are brought in contact with each other. This typically may comprise contacting sample fluid, e.g. a drop of sample fluid, with the sensor chip 1 by gravitational or capillary force. Alternatively, the sample fluid also may be actively or passively pumped towards the sensor chip 1. Contacting a sample with the sensor chip 1 thus may comprise controlling a sample providing means.

In a second step 204, the method comprises allowing interaction between the at least first dissolvable reagent layer 5 and the sample fluid, resulting in dissolving of the first dissolvable reagent layer 5 and in the interaction of at least one label 6 with the at least one target molecule. Allowing reaction between the at least a first dissolvable reagent layer 5 and the sample fluid thereby typically is allowing reaction between the at least a first dissolvable reagent layer 5 at the detection surface and the sample fluid. The latter thus allows generating free reagent at/near the detection surface 33 of the sensor chip 1. It typically enables interaction of at least one label 6 with the at least one target molecule. The method may furthermore comprise allowing interaction between other dissolvable layers and the sample fluid, thus providing other components of the interaction to be performed. Labels may be present in the dissolvable reagent layer or in another dissolvable layer, thus resulting in generating free labels for interacting with the at least one target molecule. Alternatively, labels may be provided in a different way, e.g. by introducing label-containing fluid in the sensor chip 1. Typically, in order to allow interaction between the dissolvable layers and the sample fluid, the meniscus of the sample fluid should pass over the dissolvable layer. The latter preferably requires a much smaller time span than the total assay time. Typically the wetting is performed by passing the meniscus of the sample fluid over the detection surface.

In a third step 206, detecting of a label based detection signal may be performed by any suitable detection method in accordance with the chosen labels. Envisaged suitable detection methods include optical detection methods such as, but not limited to, fluorescence detection and SERRS, and magnetic detection methods, e.g. using a Hall sensor, a GMR, TMR or AMR. Typically, the method therefore furthermore may comprise, as indicated by step 208, exciting the labels allowing to generate a label signal to be detected. Depending on the type of labels used, such exciting may for example be irradiating the sample or providing an electromagnetic field to the sample for inducing an orientation of the magnetic labels. If the exciting is an irradiating step, typically the irradiation beam used is adapted, e.g. in wavelength and/or in intensity, to be able to excite the optical labels used in the sensor chip 1. If the exciting is a step of providing an electromagnetic field, the electromagnetic field typically may be chosen such that it induces an orientation of the magnetic labels detectable with a magnetic sensor in the detection system.

The detection method 200 for detecting and/or quantifying may furthermore comprise the step of processing the label-based detection signal. The latter is illustrated by step 210. The processing may comprise obtaining a qualitative, or more preferably, a quantitative result from the label-based detection signal. The processing may be based on using predetermined algorithms, using neural networks or in any other suitable way. It may be done in an automatic and/or automated way.

In one embodiment, prior to the detection step, an optional separating step 212 may be performed for separating unbound or weakly bound labels from bound labels. The latter may be advantageous to obtain more accurate measurements, as it avoids influencing of the detection result by unbound or weakly bound labels. The removal of unbound or weakly bound labels may be ensured by removing unbound or weakly bound labels from the bound labels, bound to the detection surface via a biologically-active moiety or a tag. The latter may be performed by applying a physical or chemical force such as a flow field, acoustic field, gravitational force, electromagnetic field to move and/or remove the unbound labels. Exemplary separating techniques include rinsing, sedimentation, precipitation, centrifugation, sonication, application of magnetic and/or electric fields and field gradients.

In particular embodiments, a separation step of the bound and unbound labels may not be required. This can be achieved e.g. by the provision of a probe being a molecular beacon which comprises an oligonucleotide sequence complementary to the target DNA sequence, and which is dually labelled with a dye and a quencher (e.g. Dabcyl) at each of its two ends. In its closed state, the signal of the dye is quenched by the quencher. When the complementary sequence hybridizes to the target DNA, the beacon opens up and a signal can be detected. One example of molecular beacons are SERRS beacons which are dually labelled probes with a different dye at each of its two ends. The second dye is specifically designed such that it is capable of immobilizing the oligonucleotide probe onto a detection surface being an appropriate metal surface. In the absence of target DNA, the beacon is immobilized in the "closed state" on the metal surface, resulting in the detection of a surface-enhanced resonance Raman scattering (SERRS) spectrum corresponding to both dyes. When the complementary sequence hybridises to the target DNA, the beacon opens up and one of the dyes is removed from the surface. This causes the SERRS signals to change. In another particular embodiment where the separation of the bound and unbound labels is not required, at least two fluorescent labels may be present that form part of a fluorescence resonance energy transfer (FRET) couple, the one label being attached to the detection label and the second label being mobile in the fluid. Only when the two labels are in close proximity to each other will fluorescence at the combined wavelength of the FRET couple be detected.

The detection method 200 may also include a calibration step. Therefore, the sensor signal may be measured before and after wetting so as to calibrate the sensitivity of the sensor chip to the label and/or the thickness of the reagent layer. Such a calibration step may be performed or processed using predetermined algorithms and the results of such a calibration step may be taken into account in the signal processing step, e.g. during quantifying of the detection results.

The detection method 200 according to the present invention may be combined with magnetic extraction and a catch assay in which a solution is pre-incubated with magnetic particles. Immediately after wetting, the particles are pulled toward the sensor surface. The reagent burst can enhance the sensing process, e.g. by locally providing a biochemical condition (e.g. pH, salts, organic molecules) that optimizes the speed, sensitivity, and specificity of the (un)binding to the sensor surface.

According to a third aspect, the present invention provides a sensor chip 1 for detecting one or more analytes in a sample. More particularly, a sensor chip 1 is envisaged for use in a detection system 100 as described above. The sensor chip 1 for detecting and/or quantifying at least one target molecule in a sample may be adapted for comprising at least one label 6 for enabling label detection, and comprising a detection surface 33 for providing at least a first dissolvable layer. The first dissolvable layer 5 typically comprises at least one reagent and typically also may be referred to as dissolvable reagent layer 5. The dissolvable reagent layer 5 typically is positioned on a detection surface 33. The dissolvable reagent layer 5, when brought into contact with a sample fluid, typically enables interaction of the at least one label 6 with the at least one target molecule thus enabling detection of a label based detection signal. Other features, properties and advantages typically may be the same as described for the sensor chip in the first aspect of the present invention.

According to a fourth aspect, the present invention provides a kit of parts comprising at least one sensor chip as described in the first aspect of the present invention in combination with an amount, e.g. predetermined amount, of at least one target molecule in a buffer solution. The latter may serve as a positive control and/or as a standard. The selected at least one target molecule in buffer solution typically will depend on the type of assay to be performed with the sensor chip. Such sensor chip 1 is e.g. suitable for enzyme activity analysis of an enzyme that may convert the enzyme substrate embedded in a reagent layer on the sensor chip, although the invention is not limited thereto and may be used in for any suitable analysis or assay, as described in any of the different aspects of the present invention and/or in any of the different embodiments and/or examples provided. Optionally this kit of parts further comprises other components such as a predetermined amount of control fluid allowing for performing a negative control measurement, whereby the sensor chip specifically needs to provide a negative detection signal, indicating the absence of the target molecule tested for.

The different aspects of the present invention will now be illustrated by a number of particular embodiments and examples, the invention not being limited thereto.

In a first particular embodiment, a detection system as described above for the first aspect is provided, wherein the detection system 100 is adapted for use with at least one sensor chip 1, the sensor chip 1 comprising a first dissolvable reagent layer 5 and a second dissolvable layer. Referring in particular to the drawing of FIG. 2, a preferred embodiment of a sensor chip 1 is shown for use in accordance with the present invention. The sensor chip 1 includes a chip carrier 2 having a surface 3 comprising a detection surface 33, and a first dissolvable reagent layer 5 comprising a dissolvable matrix 7 and at least one label 6. The label 6 is provided with a probe 61. A suitable first dissolvable reagent layer 5 may typically overlie the detection surface 33 enabling close proximity of labels to the detection surface 33 thereby reducing the detection time. This first dissolvable reagent layer 5 may be contacted with the sample fluid by suitable means, e.g. by gravitational or capillary action or optionally assisted by pressure or vacuum. The detection surface 33 of the sensor chip 1 of the present embodiment is covered with a second layer 4 being a biologically-active layer e.g. comprising capture probes 41 such as antibodies or oligonucleotides, targets, or target analogues. The chip carrier 2 in the present example includes a sensing/detecting device 30 for detecting a detectable signal indicative of the analyte in the sample.

A second particular embodiment describes a detection system as described above for the first aspect, wherein the detection system is adapted for comprising at least one sensor chip 1, the sensor chip 1 comprising a first dissolvable reagent layer 5, a second biologically-active surface layer 4 and at least one third dissolvable layer. Referring in particular to the drawing of FIG. 3, a preferred embodiment of a sensor chip 1 is shown for use in accordance with the present invention. The sensor chip 1 typically may include a chip carrier 2 having a surface 3 comprising a detection surface 33, a first dissolvable reagent layer 5 comprising a dissolvable matrix 7 and at least one label 6, a second layer being a biologically-active surface layer 4, and at least one third layer being a spacing layer. Examples of the at least one third layer are shown by layer 8 and layer 9 functioning as protection layer and/or calibration and/or buffer layer. In other words, protection layers may be provided and/or layers for assisting in calibration referred to as calibration layers may be provided and/or buffer layers may be provided. It can be advantageous to apply multiple layers on the biosensor. One example may be to insert layer 8 as a buffer layer, e.g. a layer that does not contain biologically-active species, to suppress that, during fabrication of the biosensor, labels 6 bind to capture probes 41 attached to surface layer 4. Another example may be to add calibration materials to the sensor chip for allowing calibration of the detection with the sensor chip 1. Still another example is to add a cover layer 9 that acts as a protection and lift-off layer against contaminations, e.g. organic contaminants excreted by surrounding cartridge materials during processing or storage. When the sensor chip 1 is contacted with the sample fluid, the dissolvable matrix of the layer(s) typically may dissolve thereby providing reagents, labels and optionally calibrating reagents. The provision of additional layers, as illustrated in the present embodiment, may allow that the labels 6 are stored in dissolvable matrix 7 and do not become bound, during fabrication of the biosensor, to capture probes 41 attached to surface layer. The latter is preferred as biological molecules and/or bonds can change during storage and handling, e.g. causing non-specific bindings between labels 6 and the sensor surface 3 which disqualifies the biosensor for displacement/competition/inhibition or other types of assay. It therefore is an advantage of particular embodiments of the present invention that the label-to-surface bindings are substantially formed freshly during the assay with the test fluid.

Figure 4:
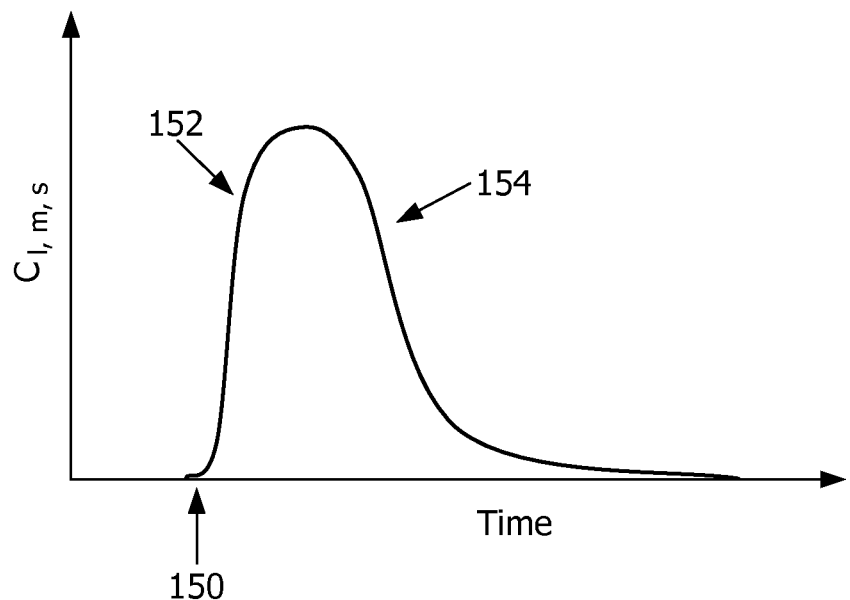
FIG. 4 is a graph of the evolution of the volumetric concentration of mobile labels near the detection surface ($C_{l,m,s}$) as a function of time as obtainable in a detection method according to a particular embodiment of the second aspect of the present invention.
Figure 5:
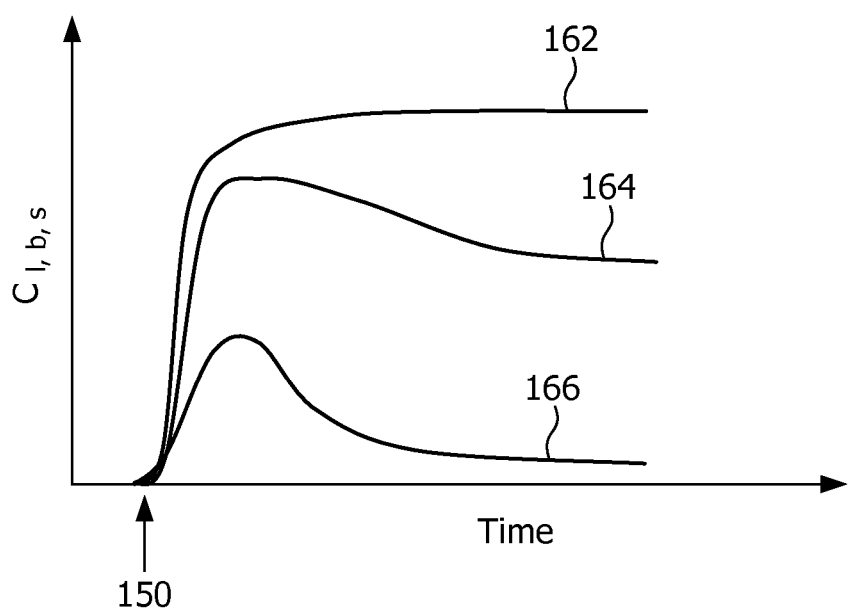
FIG. 5 is a graph of the evolution of the areal concentration of bound labels on the sensor surface ($C_{l,b,s}$) as a function of time as obtainable in a detection method according to another particular embodiment of the second aspect of the present invention.

In a third particular embodiment, a sensor chip as described according to the first aspect or according to any of the first or second embodiment is provided, the biosensor being a multilayer biosensor and the target molecule being detectable through a displacement/competition/inhibition-type assay. The sample may for example be saliva for drugs of abuse testing, the embodiment not being limited thereto. The sensor surface 3 may be provided with drug-analogues 41 at the detection surface 33. The sensor chip 1 typically comprises a first dissolvable reagent layer 5, whereby the labels 6 may be embedded in a dissolvable matrix 7 thereof The labels 6 may be provided with one or more anti-drug antibodies 61. When the sample fluid arrives on the sensor chip, the matrix 7 typically dissolves into the fluid and the labels 6 become mobile. FIG. 4 sketches the evolution of the volumetric concentration $C_{l,m,s}$ of mobile labels 6 near the sensor surface 3 as a function of time. The duration and shape of the burst peak is determined e.g. by the thickness of layer 5, the dissolution rate of the material of layer 5, and the velocity of labels 6 in the sample fluid. In FIG. 4, arrow 150 indicates the time of wetting of the detection surface and arrow 152 indicates the labels becoming mobile. Once mobile, the labels 6 are present at the sensor surface 3 in a very high concentration. The time needed for labels 6 to bind to the detection surface 33 is very short, due to the high temporary label concentration and high biological affinity of the labels 6 to the drug-analogues 41 on the detection surface 33. Arrow 154 indicates the moment the labels substantially diffuse away from the detection surface or get bound at the detection surface. Meanwhile the antibodies 61 are exposed to the drug molecules, i.e. the target molecules, in solution. When the drug molecules bind to the antibodies 61, the binding of the labels 6 to the drug-analogues 41 on the detection surface 33 weakens and/or causes dissociation of the labels 6 from the drug-analogues 41 on the detection surface 33. The time evolution of labels 6 bound to the detection surface 33 is sketched in FIG. 5 for a low, moderate, and high concentration of target molecules in solution. The sample is wetted at a first moment, indicated by arrow 150. For a given reagent layer 5 and for given labels 6, the duration and shape of the surface concentration of bound labels $C_{l,b,s}$ bound the sensor surface as function of time for different concentrations of analytes is shown in FIG. 5. Curve 162 indicates the concentration of bound labels for low concentration of analytes, indicating that the concentration of bound labels stays high. Curve 164 indicates the concentration of bound labels for higher concentration of analytes, indicating that the concentration of mobile labels drops slightly after reaching a peak. Curve 166 indicates the expected concentration of bound labels for a still higher concentration of analytes, indicating that the drop of concentration of bound labels drops stronger after reaching the peak. When the surface concentration of labels 6 is measured by a sensor, the target concentration can be derived from the time dependence of the signal and/or the signal size after a certain time. Detection of the labels 6 typically may take place at the detection surface 33 through an optical or magnetic detection method. For example, a magnetic sensor 30 such as a Hall sensor may be embedded in the carrier chip 2 for detecting the binding of a magnetic label 6 to the detection surface 33. The amount of label 6 detected is directly or conversely proportional to the amount of target molecule and hence the concentration of the target can be determined. The speed of the test is limited by the association rate between drug and antibody. For a given antibody, the probability p that a drug-antibody bond is formed increases linearly with time in the limit p<1. The probability increase per unit time dp/dt is given by $$\frac{dp}{dt} = k_{on} \cdot [T]$$

with $k_{on}$ the association constant of the binding of drug to the antibody being for example $10^5$ L·mol$^{-1}$·s$^{-1}$ for a drug-antibody bond, and [T] the drug concentration in the fluid being for example 100 nmol·L$^{-1}$ give dp/dt=0.01 s$^{-1}$. This means that after 10 s antibody-drug bonds are formed with a probability of 10%.

Figure 2:
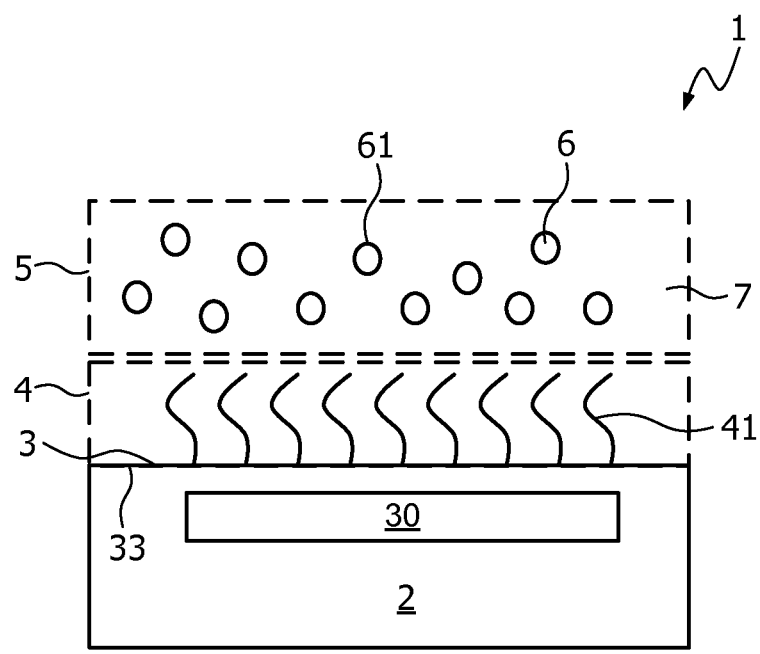
FIG. 2 is a schematic representation of a biosensor chip with dissolvable reagent layer suitable for a label-based detection system according to a particular embodiment of the first aspect of the present invention.
Figure 3:
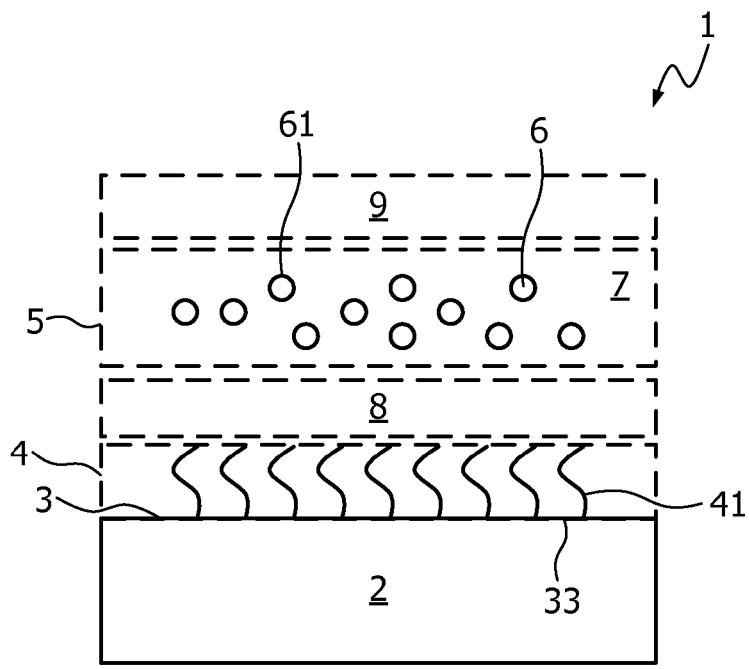
FIG. 3 is a schematic representation of a biosensor chip with dissolvable reagent layer suitable for a label-based detection system according to another particular embodiment of the first aspect of the present invention.

In a fourth particular embodiment, a sensor chip as shown in FIG. 2 is provided, the biosensor being coated with a dissolvable layer of reagents and the target molecule being detected by an enzymatic assay. The layer of reagents typically may be a thin layer as described above and a plurality of layers typically may be provided. The sample may for example be a fluid sample containing an enzyme for detecting its enzymatic activity. Generally the activity of an enzyme may be expressed in units that are defined as the amount of enzyme that is required to convert a certain amount of substrate in a certain time frame. Specific activity may also be expressed as units per volume of sample. The enzyme may be a cleaving enzyme such as a protease or a nuclease, whereby the cleaving activity may be detected. In the context of the present invention, enzymes are defined as biologically-active moieties that facilitate the cleavage e.g. by endopeptidases or endonucleases, breakdown e.g. by exopeptidases or exonucleases, or modification (e.g. by kinases or phosphatases, by oxidases or reductases) of an enzyme substrate into a product, i.e. a degradation product. The enzyme may also be a modifying enzyme such as a kinase or a phosphatase that adds or removes biochemical moieties such as a phosphate group. In other words, the target molecule also may be specifically converted by an oxidase or reductase enzyme. The enzyme thereby may e.g. be present in the thin film dried reagent on the detection surface. After wetting, the target typically is converted and one of the reaction products is detected or further processed. The modifying activity thus may be detected. Generally cleavage may result in the release of at least two product parts. The enzyme substrate may be a protein or peptide because these may easily be converted into product by an enzymatic reaction. Alternative enzyme substrates may be other biological and chemical substances such as nucleic acids, lipids, carbohydrates and chelators. An enzyme substrate may be part of the reagent layer 5 or may be immobilized onto the sensor surface 3. The reagent layer 5 typically is able to dissolve in the sample fluid to which it is exposed. A reaction occurs near the sensor surface 3, which is an indication of the activity of a specific enzyme in the fluid sample. The enzymatic conversion rate can be estimated as follows. For a given enzyme substrate in the device, the probability p that the enzyme substrate is converted by the enzyme increases linearly with time in the limit p<1. The probability increase per unit time dp/dt, given by $$\frac{dp}{dt} = k_{on} \cdot [E]$$

with $k_{on}$ the conversion constant being for example $10^6$ L·mol$^{-1}$·s$^{-1}$ and [E] the enzyme concentration in the sample fluid being for example 100 nmol·L$^{-1}$ give dp/dt=0.1 s$^{-1}$. This means that after 1 s, the enzyme substrate is converted with a probability of 10%. When the enzyme concentration [E] in the sample fluid is for example 1 µmol·L$^{-1}$, dp/dt=1 s$^{-1}$ meaning that after 1 s enzyme substrates in the vicinity of the detection surface are converted with a probability of nearly 100%. As described above, the rapid dissolution and diffusion of reagents is a burst process. When diffusion is the dominant transport mechanism, a suitable layer thickness L can be estimated from L≈√(D.t), with D the diffusion constant of the active moiety in the dissolved reagent and t the desired reaction time. When the enzyme substrate is a small protein, D is of the order of $10^{-10}$ m$^2$·s$^{-1}$ once the protein is released into the solution. With a desired reaction time of 1s, a suitable layer thickness L is about 10 µm. A much thinner layer will give a strong time dependence of the enzyme substrate concentration during the reaction process. A much thicker layer consumes an unnecessarily high quantity of reagent and furthermore generates a distribution of target molecules, for example the product of the enzymatic conversion of the enzyme substrate, that is further away from the sensor surface 3. When the enzyme is coupled to a larger entity, e.g. a nanoparticle with a size of 300 nm, D is of the order of $10^{-12}$ m$^2$·s$^{-1}$. With a desired reaction time of 10 s, a suitable layer thickness L is about 3 µm.

In a first particular example of the fourth embodiment, the reagent may comprise a labelled enzyme substrate (6, 61). The sensor surface 3 typically is coated with substrate-binding moieties 4, e.g. anti-substrate antibodies. Moieties may be embedded in a dissolvable protective layer, e.g. containing sugar molecules for hydration. After wetting the sensor chip 1 with the sample fluid, typically two events may take place concomitantly. The enzymes from the sample typically may cleave the label 6 from the labelled enzyme substrate (6, 61) thereby releasing enzyme substrate 61 and meanwhile the anti-substrate antibodies 41 on the sensor surface 3 capture both the labelled enzyme substrate (6, 61) and the (cleaved, de-labelled) enzyme substrate 61. Thus, the cleaving activity of the enzyme under investigation reduces the opportunity of labels 6 to bind to the sensor surface 3 and/or releases already bound labels 6 from the sensor surface 3.

In a second particular example of the fourth embodiment, the sensor surface 3 typically is coated with product-binding moieties 41 that selectively bind the product of the enzymatic conversion.

In a third particular example of the fourth embodiment, the enzyme substrate 61 in the reagent layer 5 is pre-coupled to a label 6 and has a tag such as biotin. The sensor surface 3 may be coated with a tag-binding moiety 41 such as streptavidin.

In a fourth particular example of the fourth embodiment, the reagent layer 5 may comprise a label 6 that is pre-coupled to a substrate-binding moiety 61 such as an anti-substrate antibody. The sensor surface 3 is coated with an enzyme substrate 41. The label 6 may be a label with a tag such as for example biotin. The sensor surface 3 typically may be coated with an enzyme substrate 41, which is provided with an accessible tag-binding moiety such as streptavidin.

In a fifth particular example of the fourth embodiment, the reagent layer 5 comprises an enzyme substrate 61 with a first and a second tag, and contains a label 6 that is provided with a moiety that can bind to the first tag. The sensor surface 3 is coated with a capture probe 41 that can bind to the second tag. Suitable tag/tag-binding couples are e.g. avidin/biotin, streptavidin/biotin, hapten/antibody, protein/antibody, peptide/antibody, protein/carbohydrate, protein/protein, nucleic acid/nucleic acid, protein/nucleic acid, hapten/nucleic acid.

In a sixth particular example of the fourth embodiment, the reagent layer 5 comprises an enzyme substrate and the product of the enzymatic conversion is detected in a competition-displacement-inhibition assay as described above.

In a seventh particular example of the fourth embodiment, the reagent layer 5 comprises an analyte-specific enzyme and a product-sensitive compound that is pre-coupled to label 6. For example, the analyte to be detected in a sample may be glucose. After wetting the sensor chip, the glucose molecules in the sample are converted by glucose oxidase present in the reagent layer 5 into hydrogen peroxide. This oxidative reaction product subsequently interacts with an oxidation-sensitive moiety, e.g. a cysteine residue embedded in a protein such as a phosphatase. An immunoassay performed with antibodies 41 which are sensitive to the oxidation state of the oxidation-sensitive moiety, indicates the glucose level in the fluid sample.

In another example, the analyte to be detected has a regulatory effect in an enzymatic conversion and is e.g. a promotor, activator, inhibitor, or cofactor. The dry reagent multilayer comprises an enzyme and an enzyme substrate. After wetting the biosensor, the enzyme and enzyme substrate are dispersed into solution. Subsequently, the enzyme product is generated at a rate that depends on the concentration of the analyte in the solution. The product can then be detected. Preferably, the enzyme substrate is pre-coupled to a detection label 6 and the detection surface 33 is provided with anti-product antibodies 41. Alternatively, a product-analogue is pre-coupled to a detection label 6 or to the detection surface 33. Preferably, the detection label 6 is a magnetic particle.

In another example, product-binding moieties 61 are pre-coupled to the labels 6 and product-analogue 41 is present on the sensor surface 3. In a further example, product-analogue 61 is pre-coupled to the labels 6 and the sensor surface 3 is coated with product-binding moieties 41. As mentioned above, also architectures with one or more tags are possible.

In another, preferred, embodiment use is made of magnetic actuation during the dispersion process. This process is also referred to as re-suspension or re-dispersion process. In this embodiment, dried reagents are dispersed while magnetic actuation is applied during and/or after re-dispersion. In a most preferred embodiment reagents coupled to magnetic particles are attracted to the sensor surface by applying a magnetic field. This magnetic actuation was found to speed up the binding process to the sensor surface. Optionally in another actuation step, unbound or non-specifically bound magnetic beads are subsequently removed from the sensor surface. This magnetic actuation can be carried out suitable with a sensor chip and reader system comprising a system for magnetic actuation positioned at one side of the sensor surface and a second magnetic actuation system positioned at the other side of the sensor surface.

In still another example, the target molecule is a small organic molecule, typically too small to be detected with available capture molecules such as antibodies. The reagent layer then may comprise enzymes and suitable fusion moieties such that after wetting, the enzyme generates a substrate-target complex that can be more easily detected, e.g. using antibodies with specificity to the substrate-target complex.

According to a fifth embodiment of the present invention, the analyte of interest is a nucleotide and the methods of the invention involve the use of at least one labelled analyte-specific probe which is a nucleotide probe, of which the sequence is complementary or similar to at least part of the analyte of interest, most particularly a sequence of the analyte which is specific for the analyte. This nucleotide probe is bound to a label to allow specific detection of the analyte as described above. Temperature control may be included in detection systems for the detection of nucleotides such that the thermal conditions can favour hybridization reactions appropriately.

In yet another particular embodiment according to any of the embodiments as described above, a dissolvable layer on a sensor chip may comprise a known amount of target molecules or target analogues for on-chip assay calibration. The latter allows to calibrate the sensor chip, thus allowing to obtain more accurate results.

In another particular embodiment according to any of the embodiments as described above, a dissolvable layer 4, 5 on a sensor chip may comprise inactive moieties 41, 61 and/or an inhibitor and/or a blocking agent.

In another particular embodiment according to any of the embodiments as described above, a dissolvable layer on a sensor chip may comprise capture probes 41, 61 that are mutually biologically-active but do not have an activity to components normally present in the sample to be investigated.

In another particular embodiment according to any of the embodiments as described above, a dissolvable layer on a sensor chip may comprise at least one component of which the biochemical activity is reduced, e.g. due to a folding, shielding, capping, or masking condition, or due to the presence of a protective agent. A protective agent can e.g. serve to preserve the component during processing, storage and handling. A dissolvable layer on a sensor chip may also comprise an activation enzyme, e.g. to reverse the action of the protective agent. For example, when the surface is wetted, this activation enzyme is dispersed in the solution and activates the biologically-active component.

Different embodiments of the present invention allow for a large number of useful bioassays to be run in a fast and cost-effective manner. Multiple chromogenic labels may be used as in micro-array technology, flow cytometry, detection based on fluorescence resonance energy transfer (FRET) which occurs due to the interaction between the electronic excited states of two chromogenic dye molecules, molecular beacons based detection technology such as e.g. real-time nucleic acid detection and real-time PCR quantification, surface enhanced detection techniques such as surface-enhanced Raman spectroscopy (SERS), surface-enhanced fluorescence (SEF) or surface-enhanced resonance Raman spectroscopy (SERRS), microfluidic detection, etc. In some embodiments, the detection system of the present invention is an epi-fluorescence biosensor meaning that excitation light is incident on the surface from above, but it could also be a transmission biosensor, meaning that excitation light is incident from below and transmitted through the biosensor.

The invention further provides a method for preparing a system according to this invention the method comprising the steps of a) providing a sensor chip with a detection surface b) contacting the surface with a fluidic composition comprising reagent, wherein the fluidic composition is a buffer composition that is essentially free of surfactant, c) drying the buffer composition with reactant to form a layer on the detection surface. It was surprisingly found that the use of a drying buffer composition that is essentially free of surfactants such as Tween, results in increased specific binding of target compounds such as magnetic particles to the sensor surface. In this context, essentially free of surfactants means less than 0.01%, more preferred less than 0.001% surfactant, more preferred less than 0.0001% surfactant.

The present invention also provides a solid-state microtechnology which is suitable for high-parallel microfabrication and high-parallel processing. This allows for multiplexing in a diagnostic assay. The technology enables rapid screening of reagent variables, e.g. layer thickness, reagent composition, combinations of different layers. Detection can occur with sensors integrated into the chip carrier or monitoring with an external instrument (e.g. optical imaging).

An advantage of particular embodiments of the present invention is that optimal assay conditions are created instantly upon contacting the sample fluid and dissolving the reagent layer(s) which reduces assay time and improves assay sensitivity and specificity. It is an advantage of particular embodiments of the present invention that cost-effective detection is obtained, e.g. due to the provision of thin reagent layers and the resulting requirement for minimal amounts of reagents.

It is an advantage of particular embodiments of the present invention that there may be a fresh formation of a capture layer on the sensor or on the label during the assay. The reagent can for example contain a capture or detection moiety with a tag, e.g. a biotinylated antibody or a biotinylated molecular beacon, while the label or sensor contains a tag-binding moiety. The fresh formation of biological complexes can have advantages for short-lived complexes and for complexes that are prone to non-specific bonds at longer time scales (e.g. particle clustering, non-specific binding to the sensor surface).

It is an advantage of particular embodiments of the present invention that a biosensor is provided with a thin layer of reagents on the sensor surface. When the sensor chip is wetted by a fluid, the reagents dissolve rapidly and the sensor surface is exposed to a burst of reagents, i.e. the sensor surface is shortly exposed to a high concentration of reagents. Due to the thin layer and high speed of the assay, an array of sensors can be made with different reagents and independent assays. The application of multiple layers can allow on-chip assay calibration. The proposed biosensor has potential for fast assays, low reagent use, multiplexing, calibration, and small sample volume. In other words, short assay times and substantially instant label detection may be obtained It is an advantage of particular embodiments of the present invention that detection of small organic molecules in magnetic biosensors is made possible. Typically, small organic molecules may be too small to be detected with available capture molecules such as antibodies, whereas due to enzymatic modification, e.g. fusion, detectable complexes are obtained. By providing the enzyme and/or suitable fusion moieties in the reagent layer, sensitive and rapid detection can be obtained.

Other arrangements for accomplishing the objectives of a biosensor with dissolvable reagent layers embodying the invention will be obvious for those skilled in the art. It is to be understood that although preferred embodiments, specific constructions and configurations, as well as materials, have been discussed herein for devices according to the present invention, various changes or modifications in form and detail may be made without departing from the scope and spirit of this invention.

The invention is illustrated by the following non-limiting examples.

EXAMPLE 1

As a model system, a morphine competition assay was used, in which morphine from the sample fluid competes with morphine immobilized on the sensor surface for the binding sites on magnetic particles coupled to anti-morphine antibodies. Frustrated total internal reflection (FTIR) was used for detection of the MPs on the sensor surface made of injection-moulded Cyclo Olefin Polymer (COP/Zeonex) FTIR is suitable for real time monitoring magnetic particle binding on the sensor surface.

Buffers and Reagents

MES saline buffer (25 mM MES, 150 mM NaCl, 2 mM EDTA, 0.05% Tween20 pH7.4), Borate buffer (50 mM Sodium Borate, 0.05% Tween20, pH 9), Coating buffer (15 mM Sodium carbonate, 35 mM Sodium bicarbonate, 0.05% Na-azide, pH9.6), Drying Buffer (50 mM TRIS-HCl, 1%/5% BSA, 5% Trehalose/Sucrose), Re-dispersion buffer (50 mM Tris-HCl, 0.1% BSA, 0.05% Tween20 pH 8) or (76 mM Na2HPO4, 4 mM KH2PO4, 400 mM NaCl, Azide, 0.1% TritonX405, pH8). BSA-morphine solution (10 µg/mL BSA-morphine in 15 mM Na2CO3, 35 mM NaHCO3, 0.03% NaN3 at pH 9.6) and anti-morphine antibodies 1 mg/mL were kindly provided by Cozart Bioscience (Oxfordshire, UK). Carboxyl-Adembeads 300 nm and Storage Buffer were purchased from Ademtech (Pessac, France). EDC (N-3-dimethy-laminopropyl-N-ethylcarbodimide hydrochloride) and NHS (N-hydroxysuccininmide) were purchased from Pierce (IL, USA).

Substrate

The experiments were done on Cyclo Olefin Polymer (COP/Zeonex) and polystyrene injection-moulded substrates of transparent plastic with a refractive index of about 1.52. Aqueous solutions show a high contact angle on these substrates (over 90°), which indicate the hydrophobic character of the surface, which allows for a well-defined positioning of the solutions.

Bioconjugations

Carboxyl-Adembeads (Ademtech) 300 nm Magnetic Particles were washed two times in one volume of MES saline buffer using a magnetic particle concentrator (Dynal MPC-1, Magnetic Particle Concentrator, Dynal Biotech ASA). The beads were re-suspended in MES saline buffer at 10 mg/mL (1% solid weight). In order to activate the carboxyl groups, the beads were incubated at 37° C. for 30 minutes shaking at 1000 RPM (Thermomixer Comfort, Eppendorf, USA) with 40 mg/mL EDC and 40 mg/mL NHS mixed 1:1 in $H_2O$. The activated beads were washed once with MES saline buffer, once with Borate buffer and finally re-suspended in Borate buffer at 10 mg/mL. Before coupling, in order to avoid aggregation, the beads were sonicated 3 times 3 seconds with 40% amplitude using a sonicator probe (VCX 130, Sonics Vibra-Cell, Sonics & Materials, Inc. USA). Anti-morphine antibodies were added to the beads solution at 2.8 μg/mL and incubated ON shaking at 1000 RPM at 20° C. and sonicated thereafter 3 times 3 seconds with 40% amplitude using the sonicator probe. To inactivate remaining active carboxyl groups, the beads were incubated with 0.1M glycine for 30 min shaking at 1000 RPM at 20° C. The coated beads were washed with Borate buffer for 2 times then are transferred to a new test tube and washed the final time with two volumes of Storage buffer. The beads were stored in storage buffer at 10 mg/mL at 4° C.

Assay

Surface coating. Polystyrene substrates were coated overnight, in a humidified atmosphere at 4° C. with 2 μL of 10 μg/mL BSA-morphine in Coating buffer. After incubation, the surface was air-dried after washing 3 times with 100 μL of PBS.

Drying process. Magnetic beads coupled to anti-morphine antibodies were re-suspended by vortexing and an aliquot was transferred to a clean test tube. The beads were washed three times in Drying buffer using the magnetic particle concentrator. The beads were re-suspended in a 2% final concentration in Drying buffer of which 1 μL was deposited on top of the BSA-morphine coating. The drying process has been carried out using silica bags inside a close box overnight.

Re-dispersion process. The dried reagents were re-dispersed by adding 13 μL of assay buffer. After re-dispersion, the magnetic particles were attracted to the surface by applying a magnetic field using an electromagnet underneath the sensor surface to speed up the binding process. The unbound beads were removed from the surface using an electromagnet placed above the surface. The re-dispersion process, the binding and the washing of MPs to the surface was followed by optical imaging.

3. Results

Experiments were performed on ultra-fast morphine competitive assay with a very thin layer of dry reagents on the substrate surface. For these experiments, a 2% antibody-couple magnetic particle solution was dried on top of a BSA-morphine coated polystyrene substrate.

Re-suspension of a 2% magnetic particles (MP) layer (2% MPs coupled to anti-morphine antibodies in 1% BSA, 5% Trehalose, 50 mM Tris at pH 8.5) in buffer containing 0 ng/ml morphine resulted in MP binding to the sensor surface during re-dispersion. It was found that magnetic actuation after re-dispersion led to an increase in binding of MPs to the surface. These bindings were found to be specific, as shown by the difference in amount of MPs that retained on the surface between re-suspension, actuation and magnetic washing in buffer without morphine compared to re-suspension, actuation and magnetic washing in buffer containing 10 ng/ml morphine.

The results showed that for antibodies coupled to superparamagnetic nanoparticles deposited on an antigen coated surface, two reacting layers can be deposited on top of one another without reacting to each other. Furthermore, an ultra-fast (seconds) re-dispersion assay principle is shown, which renders an easy to fabricate bio-layer deposition method useful for biosensors that require short assay times.

Figure 7:
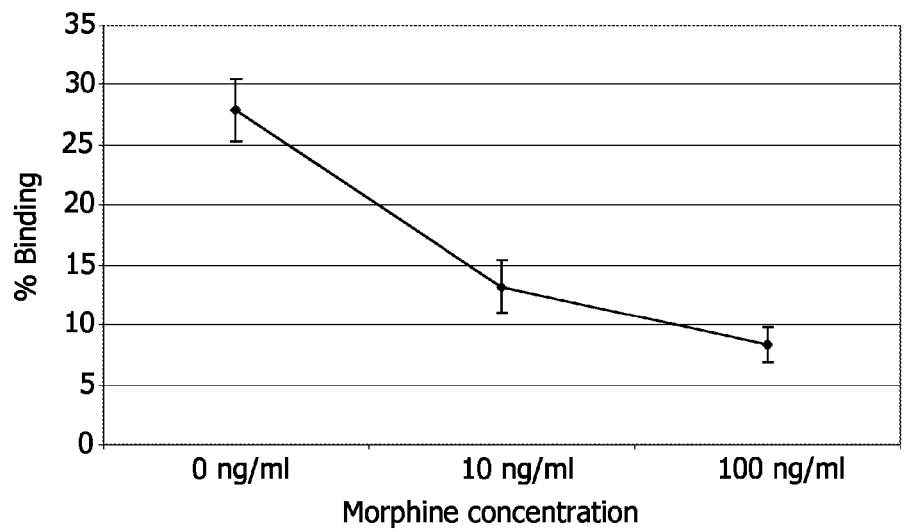
FIG. 7 shows the results of a morphine competition assay in a method according to the present invention

FIG. 7 shows a dose-response curve of morphine concentration versus the optical signal difference due to MP binding. It was observed that re-dispersion of MPs in a solution containing morphine showed a dose dependent decrease in optical signal after re-dispersion actuation and magnetic washing. These results indicate that this assay setup, is very suitable for deposition of an antibody-coupled MP layer directly on a functionalised substrate surface.

EXAMPLE 2

As a model system, the morphine competition assay was used, in which morphine from the sample fluid competes with morphine immobilized on the sensor surface for the binding sites on MPs coupled to anti-morphine antibodies. Frustrated total internal reflection (FTIR) was used for detection of the MPs on the sensor surface made of injection-moulded Polystyrene For these experiments, polystyrene substrates were coated overnight, in a humidified atmosphere at 4° C., with 2 μl BSA-morphine solution (10 μg/ml BSA-morphine in 15 mM $Na_2CO_3$, 35 mM $NaHCO_3$, 0.03% NaN3 at pH 9.6). After incubation, the surface was washed 3 times with 1 ml of $H_2O$ and 1 μl of 1% w/v MPs coupled to anti-morphine antibodies was deposited on top of the BSA-morphine coating. The beads were previously diluted 1:1 in drying buffer (1% BSA, 5% Trehalose, 50 mM Tris at pH 8.5) with or without the presence of 0.1% non-ionic surfactants (Tween20). The drying process of the MPs has been carried out in dried conditions (silica bags) for twelve hours. A top fluidic cartridge was glued on top of the optical cartridge and the re-dispersion of dried reagents was done by adding 13 μl of assay buffer ($Na_2HPO_4$ 10.76 g/L, $KH_2PO_4$ 0.577 g/L, NaCl 23.38 g/L, 0.01% Na-azide). The optical signal has been monitored for one minute using a CCD camera setup.

Figure 8:
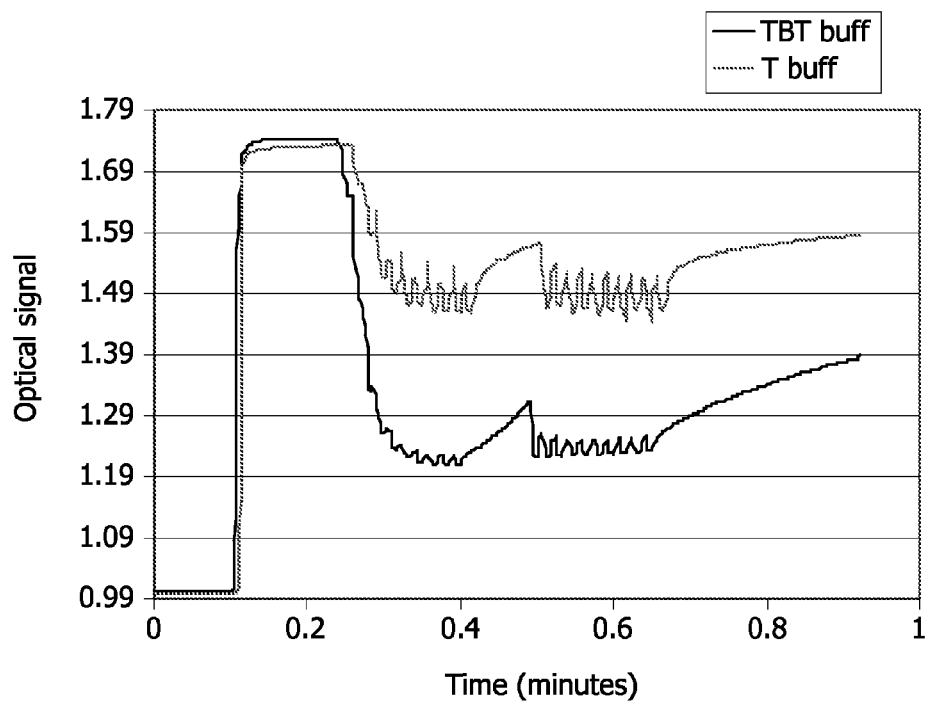
FIG. 8 shows the effect of surfactant in the drying buffer on the morphine competitive assay based on the invention.

FIG. 8 shows the FTIR signal during re-dispersion, actuation and magnetic washing. It was observed that the speed and level of re-dispersion of 1% MP-dried layer is comparable for both drying buffers and is close to 90%. This calculation can be obtained measuring the optical signal of the clean untreated surface and comparing with the area where the beads are deposited.

During the attraction step, MPs dried in TBT buffer (buffer without Tween20™) reach the surface in higher amount with respect to MPs dried in T buffer (with Tween20™) where a very low concentration of beads is present at the surface. It is important to notice that more beads are attracted to the functionalized surface and more beads have the chance to bind to the antigen.

The invention claimed is:

1. A detection system for detecting at least one target molecule in a sample fluid, the detection system comprising:
at least one sensor chip comprising a detection surface having
one of a target molecule immobilized to the detection surface and a capture molecule for the target molecule immobilized to the detection surface, and
a first dissolvable layer including a labeled target binding molecule overlaying the one of the immobilized target molecule and the immobilized capture molecule.

2. The detection system according to claim 1, further comprising a detector for detecting at least one detectable signal indicative of the at least one label.

3. The detection system according to claim 2, wherein the detector is selected from at least one of a magnetic and optical detector.

4. The detection system according to claim 1, wherein the first dissolvable layer has a thickness between 1 μm and 50 μm.

5. The detection system according to claim 1, wherein the sensor chip further comprises at least a calibration layer for providing calibration reagents, the calibration layer being a dissolvable layer adapted for enabling calibration.

6. The detection system according to claim 1, wherein the sensor chip further comprises a second dissolvable layer positioned to provide protection to the first dissolvable layer, the first dissolvable layer being sandwiched between the second dissolvable layer and the detection surface.

7. The detection system according to claim 1, wherein the system comprises an actuation system.

8. The detection system according to claim 1, wherein the system comprises a magnetic actuator.

9. The detection system according to claim 1, further comprising a sensor for determining the time of arrival of the sample fluid on the detection surface.

10. The detection system according to claim 1, further comprising a sensor adapted for measuring a volume of the sample fluid or a part thereof.

11. The detection system according to claim 1, wherein the detection surface is a porous surface.

12. The detection system according to claim 1, wherein the at least one label is a target-specific label.

13. The detection system according to claim 1, wherein the first dissolvable layer is a reagent layer including an amount of surfactants that is less than 0. 0001%.

14. The detection system according to claim 13, wherein the amount of surfactants is less than 0.0001%.

15. The detection system according to claim 13, wherein the amount of surfactants is less than 0.001%.

16. The detection system according to claim 1, wherein the label is a magnetic particle.

17. The detection system according to claim 1, wherein the first dissolvable layer comprises a labeled target binding molecule wherein the labeled target binding molecule is an antibody.

* * * * *